United States Patent
Kotra et al.

(10) Patent No.: US 9,908,853 B2
(45) Date of Patent: Mar. 6, 2018

(54) INHIBITORS OF PEPTIDYL ARGININE DEIMINASE (PAD) ENZYMES AND USES THEREOF

(71) Applicants: University Health Network, Toronto (CA); The Hospital for Sick Children, Toronto (CA)

(72) Inventors: Lakshmi Kotra, Toronto (CA); Mario Moscarello, Toronto (CA)

(73) Assignees: THE HOSPITAL FOR SICK CHILDREN, Toronto (CA); UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 14/418,570

(22) PCT Filed: Aug. 1, 2013

(86) PCT No.: PCT/CA2013/050597
§ 371 (c)(1),
(2) Date: Jan. 30, 2015

(87) PCT Pub. No.: WO2014/019092
PCT Pub. Date: Feb. 6, 2014

(65) Prior Publication Data
US 2015/0252006 A1   Sep. 10, 2015

Related U.S. Application Data

(60) Provisional application No. 61/678,134, filed on Aug. 1, 2012.

(51) Int. Cl.
| | | |
|---|---|---|
| *C07D 233/74* | (2006.01) | |
| *C07D 233/76* | (2006.01) | |
| *C07D 233/78* | (2006.01) | |
| *C07D 403/06* | (2006.01) | |

(52) U.S. Cl.
CPC ......... *C07D 233/78* (2013.01); *C07D 233/74* (2013.01); *C07D 233/76* (2013.01); *C07D 403/06* (2013.01)

(58) Field of Classification Search
None
See application file for complete search history.

(56) References Cited

U.S. PATENT DOCUMENTS

| | | |
|---|---|---|
| 3,642,836 A | 2/1972 | Cusic et al. |
| 3,770,763 A | 11/1973 | Cusic et al. |
| 3,917,636 A | 11/1975 | Cusic et al. |
| 3,997,572 A | 12/1976 | Cusic et al. |
| 4,073,924 A | 2/1978 | Sonntag |
| 4,073,926 A | 2/1978 | Sonntag et al. |
| 4,189,587 A | 2/1980 | Holt et al. |
| 4,684,736 A | 8/1987 | Topfl |
| 4,691,021 A | 9/1987 | Wang et al. |
| 2015/0118179 A1* | 4/2015 | Liu ..................... C07D 403/12 424/78.29 |

FOREIGN PATENT DOCUMENTS

| | | |
|---|---|---|
| CA | 2063671 C | 3/2005 |
| CH | 672220 A3 | 11/1989 |
| JP | 35017232 B | 11/1960 |
| JP | 03191075 A | 8/1991 |
| JP | 2002296739 A | 10/2002 |
| TR | 2005002219 A2 | 1/2007 |
| WO | 99/01428 A1 | 1/1999 |
| WO | 9905117 A1 | 2/1999 |
| WO | 2003043988 A1 | 5/2003 |
| WO | 2007014229 A2 | 2/2007 |
| WO | 2008030412 A2 | 3/2008 |
| WO | 2009127048 A1 | 10/2009 |
| WO | 2011066544 A2 | 6/2011 |

OTHER PUBLICATIONS

Ito et al. in Cancer Science 94(1), 3-8 (2003).*
STN Registry Database entry for CAS RN 1311654-48-4, dated Jul. 7, 2011.*
STN Registry Database entry for CAS RN 1061888-87-6, dated Oct. 16, 2008.*
STN Registry Database entry for CAS RN 1427898-40-5, entry date Apr. 11, 2013; Accessed Sep. 27, 2016.*
STN Registry Database entry for CAS RN 1444152-84-4, entry date Jul. 16, 2013; Accessed Sep. 27, 2016.*
National Center for Biotechnology Information. PubChem Compound Database; CID=47164586, https://pubchem.ncbi.nlm.nih.gov/compound/47164586 (accessed Jan. 30, 2017).*
NINDS, Creutzfeld-Jakob Disease Information Page, <www.ninds.nih.gov/disorders/cjd/cjd.htm> Accessed Aug. 11, 2012.*
"Alzheimer's disease." CNN Health, Obtained Oct. 9, 2010, URL:http://www.cnn.com/2003/HEALTH/conditions/09/24/alzheimers.drug.ap/index.html.*

(Continued)

*Primary Examiner* — Alicia L Otton
(74) *Attorney, Agent, or Firm* — Bereskin & Parr LLP/S.E.N.C.R.L., S.R.L.; Patricia Folkins

(57) ABSTRACT

The present application relates to imidazolidineclliones, compositions comprising these compounds and their use, in particular for the treatment of diseases, disorders or conditions characterized by or associated with the hypercitrullination of proteins by peptidyl arginine deiminase (PAD) enzymes. In particular, the present application includes compounds of Formula I, and compositions and uses thereof: (I).

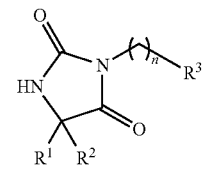

(I)

21 Claims, 13 Drawing Sheets

(56) References Cited

OTHER PUBLICATIONS

Antonio R. Damasio, Alzheimer's Disease and Related Dementias, Cecil Textbook of Medicine, 20th edition (1996), vol. 2, pp. 1992-1996.*
Wang et al., J. Immunol. 2007, 179, pp. 5958-5965.*
International Search Report and Written Opinion of PCT/CA2013/050597 dated Feb. 3, 2015.
Kireche, M. et al., Evidence for chemical and cellular reactivities of the formaldehyde releaser bronopol, independent of formaldehyde release, Chem. Res. Toxicol., 2011, 2115-2128, 24.
Zejc, A. et al., Mannich bases derivatives of physiologically active compounds X N-alkylaminomethyl derivatives of 5-methyl-5-(1,2-dibromo-2-phenylethyl)- and 5-methyl-5-styrylhydantoin, Diss. Pharm. Pharmacol., 1968, 20(1), 53-61, Abstract only.
Sato, M. The reaction of hydantoins with acrylonitrile. Nippon Kagaku Zasshi, 1962, 83, 318-323, Abstract only.
Extended European Search Report of corresponding European Patent Application No. 13825079.0 dated Feb. 26, 2016.
Todorov, Petar T., et al., "Synthesis of Phosphorus-Containing Dipeptide Mimetics via the Kabachnik-Fields Reaction", Heteroatom Chemistry, vol. 22, No. 5, 2011, pp. 669-672.
Winstead, Meldrum B., et al., "Substitution in the Hydantoin Ring. I. N-3 Aminomethyl Derivatives", Journal of Medicinal Chemistry, vol. 8, No. 1, 1965, pp. 117-120.

* cited by examiner

A.

B.

A.

B.

A.

B.

A

B

A

B

INHIBITORS OF PEPTIDYL ARGININE DEIMINASE (PAD) ENZYMES AND USES THEREOF

RELATED APPLICATIONS

This application is a National Stage of co-pending International Application No. PCT/CA2013/050597 filed Aug. 1, 2013 which claims the benefit of priority of U.S. Provisional Patent Application No. 61/678,134 filed on Aug. 1, 2012, the contents of which are incorporated by reference in their entirety.

FIELD

The present application relates to imidazolidinediones, compositions comprising these compounds and their use, in particular for the treatment of diseases, disorders or conditions characterized by or associated with the hypercitrullination of proteins by peptidyl arginine deiminase (PAD) enzymes.

BACKGROUND

Demyelination and Multiple Sclerosis.

Demyelination is a neuropathological state where the insulating myelin sheath on the axons of the neurons is degraded, the pathogenesis of which could be due to a variety of causes.[1] Multiple sclerosis (MS), one such clinical condition, is a chronic and most common demyelinating disease, affecting about 2.2 million people worldwide.[2] It is characterized by a patchy degradation of myelin on the axons, known as demyelinated lesions, and the healing of these patches occurs via scar formation called plaques.

A variety of causes such as genetic, immunological and environmental factors are suggested to play a role leading to this condition.[3] The most common theory is the autoimmune theory which postulates that sensitization of T cells in the periphery leads to their travel through a disrupted blood brain barrier to attack and destroy myelin.[4] Several CNS proteins have been shown to induce this condition, including myelin proteolipid protein (PLP),[5] myelin-associated glycoprotein (MAG),[6] myelin oligodendrocyte glycoprotein (MOG),[7] transaldolase and S100.6 Genetic studies indicate the involvement of about 30 single-nucleotide polymorphisms (SNPs), although it remains to be seen as to the relevance of these SNPs for MS therapeutics development.

Current MS therapies reduce the frequency of relapses but do not delay the progression of the disease nor do they reverse the destruction of myelin.[9,10,11] The most popular treatment is Copaxone™ (also known as Copolymer-1, Cop-1, or Glatiramer acetate), marketed by Teva Pharmaceuticals. This is an immunomodulator drug and is a random polymer of four amino acids, glutamic acid, lysine, alanine and tyrosine in the same proportion found in myelin basic protein (MBP).

The mechanism by which Copaxone™ exerts its effects in MS patients is not completely understood. However, it is believed to act by modifying immune processes that may be responsible for the pathogenesis of MS. Studies in vitro and in vivo suggest that upon administration, Copaxone™-specific suppressor T cells are induced and activated in the periphery.[12,13] There are several side effects associated with Copaxone™, and this drug is not completely effective in delaying the onset of severe or fulminating MS.[11]

Another popular drug is cannabis extract (dronabinol) used by MS patients due to its pain relief effects. A clinical study in the UK (the CUPID study) to determine the ability of dronabinol to slow disease progression in primary progressive and secondary progressive MS is currently underway.

Other clinical trials, for example, involving fingolimod (Gilenya™ by Novartis) to test safety and effectiveness of this drug in primary progressive MS, laquinimod vs. interferon β-1a (Avonex®) vs placebo to assess the compound in relapsing-remitting MS and teriflunomide (HMR1726) to assess the compound in clinically isolated syndrome (CIS), for relapsing-remitting MS, are actively being pursued in various late stages.[11]

A much anticipated oral therapy cladribine (Movectro™) for the treatment of relapsing forms of multiple sclerosis has been recently withdrawn from clinical trials by Merck Serono due to its inability to meet U.S. FDA requirements.[14,15] Cladribine—an immunomodulator—was believed to work by interfering with the activity of white blood cells in the central nervous system, thereby interrupting the immune attacks that cause the unpredictable symptoms of MS. It must be noted that cladribine in injectable form is used to treat hairy cell leukemia, thus raising severe safety concerns for long term use in MS patients simply based on its molecular mechanisms of action.

Currently, there is a desperate need for novel mechanisms of preventing and potentially reversing demyelination, such that the treatment options for demyelinating diseases such as multiple sclerosis can be conceived with better safety profiles and with clear molecular mechanisms of action.

Citrullination and Demyelination.

In general, immunological self-tolerance is an important defense against many autoimmune diseases and its breakdown in the body leads to various autoimmune diseases. This primarily arises from the immune recognition of self-proteins that have undergone post-translational modifications under pathophysiological conditions that would not happen under normal circumstances.

Citrullination, a post-translational event, in general is involved in many cellular processes such as gene regulation, embryonic development and differentiation.[16,17] Lately, the abnormal role of (hyper)citrullination in a variety of diseases has been uncovered, including in MS, rheumatoid arthritis, Alzheimer's, scrapie, psoriasis and Creutzfeld-Jacob disease.[18,19] Thus the generation, metabolism and regulation of citrullinated proteins have become a major focus of research.[20,21] For example, deimination (or citrulination) of histone H3 is correlated to apoptosis of human neural stem cells, and inhibition of citrullination showed reduced apoptosis and less tissue loss as well as enhanced regeneration of neural cells.[17]

In MS, extensive studies of hypercitrullinated MBP indicated that MBP, a key component of the myelin sheath and critical for the maintenance of myelin compaction, contained the non-coded amino acid citrulline in abnormal proportions. In normal brain, the "citrullinated MBP" accounts for 20% of the total MBP, whereas in chronic MS it accounts for 45%[22] and in fulminating MS it is 90% of the MBP.[23] In a number of studies using a variety of biophysical techniques,[24,25,26,27,28] it was demonstrated that citrullinated MBP prevented compaction of the bilayer, resulting in destabilization of the membrane and subsequent degradation leading to demyelination, and an irreversible damage to the axons.[29,30]

Thus, hypercitrullination is at the root of neuropathogenesis due to demyelination. In the central nervous system, peptidyl arginine deiminases (specifically PAD2 and PAD4) are responsible for the citrullination.

PAD Enzymes and Citrullination.

Peptidyl arginine deiminase (PAD) catalyzes the post-translational citrullination of proteins.[31, 32, 33] Citrullination is the process of deimination of Arg residues on select proteins, or in other words, transformation of Arg into citruline via deimination (Scheme 1). There are five isozymes of PAD that exist in humans: PAD-1, -2, -3, -4 and -6. Their expression in tissues varies significantly, regulated by transcriptional and post-transcriptional mechanisms. PAD2 and PAD4 are specifically implied in multiple sclerosis, as enhanced levels of these two isoforms are observed in CNS under inflamed conditions.[21,34,35]

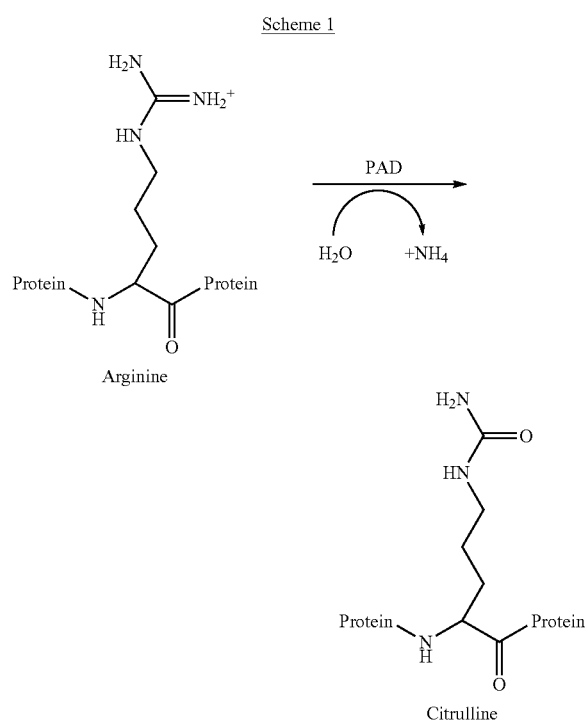

Scheme 1

There is convincing evidence in vivo that higher levels of PAD activities and hypercitrullination are observed in MS.[36] For example, a routinely used MOG-EAE model for MS, which is a CD4(+) T cell-driven model, induced with the immunodominant 35-55 peptide of myelin oligodendrocyte glycoprotein (pMOG35-55) was used to test whether citrullination of a T cell epitope can contribute to disease etiopathology.[29,37] In this experimental model, the PAD2 and PAD4 enzymes were significantly upregulated in the inflamed CNS of the animals. T cells that responded specifically to the citrullinated pMOG could not initiate the EAE lesion, but these cells could provoke exacerbation of pathology if transferred into mice with an ongoing EAE. This experiment strongly suggested that once inflammation in MS is established, citrullination of target autoantigens can allow an expanded repertoire of T cells to contribute to CNS pathology, and enhanced levels of PAD enzymes are observed in these tissues.[37] A similar study using the peptides from myelin basic protein (MBP) epitopes indicated that self-antigens could potentially trigger the disease in susceptible individuals carrying citrullinated peptide epitopes.[38,39]

In an elegant study by Oguz et al., it was shown that citrulline is more frequently identified in the brains of patients in vitro with an early onset of the MS disease than in the healthy subjects using magnetic resonance spectroscopy.[40] This study and others established the direct correlation between hypercitrullination and the disease progression in MS.[41]

Raijmakers et al. reported that PAD2 knockout mice developed EAE despite the lack of PAD2 which suggested hypercitrullination may be irrelevant in MS.[42] However, the Moscarello group collaborated and obtained these PAD2 knockout mice from Raijmakers' lab, extracted MBP from whole brain digested with trypsin and resolved the peptides by mass spectrometry. Several citrulline-containing MBP peptides were discovered and confirmed that citrullinated MBP was present in the PAD2 knockout mice.[44] In addition, citrullinated CNPase (cyclic nucleotide phosphohydrolase, a myelin enzyme) and MOG (myelin oligodendrocyte glycoprotein) were also detected in these samples. The citrullinated MBP was generated by PAD4 that is present in the brain and spinal cord (as does PAD2, if it were present). The PAD2 knockout mice contained similar amounts of PAD4 as the wild type mice.[44] In summary, protein citrullination is an active process in the PAD2 knockout mice due to PAD4 activity. Thus, investigations on deiminases and the inhibition of PAD2 and PAD4 enzyme activities are important challenges in pursuit of understanding demyelinating diseases.[21,43,44,45]

Inhibitors of PAD Enzymes:

A non-specific, active site PAD inhibitor, 2-chloroacetamidine (2CA), attenuated MS disease, decreased the amount of citrullinated protein and decreased PAD activity in the brain in four animal models of MS: two neurodegenerative and two autoimmune disease models.[46]

Protein citrullination, expression of PAD protein and the corresponding enzyme activity in extracts of normal and of normal-appearing white matter (NAWM) from MS patients have been investigated (FIG. 1).[47] PAD2 protein expression was elevated in NAWM from MS brain, with a corresponding increase of PAD activity and protein citrullination (FIG. 1A).[48] Since PAD4 translocates into the nucleus and affects the transcription, it was of interest to look at PAD2 mRNA levels after treatment with 2CA. A decrease in the mRNA levels indicates the potential inhibitory effect of 2CA on PAD4 activity. The elevated activity of PAD in normal-appearing white matter is 2-4 fold that in the normal tissue. These levels of PAD also correlate well with the elevated levels of citrullinated protein in the white matter of the MS patients, in comparison to that in normal brain white matter (FIG. 1B). Following the addition of 2CA to NAWM extracts, PAD activity declined, demonstrating that 2CA was effective in human brain extracts dampening the enzymic activity of PAD (FIG. 1C), although 2CA is a non-specific inhibitor. 2CA targets all PAD isozymes since it's a non-specific inhibitor.

2CA is a covalent inhibitor of PAD4 (FIG. 2). This inhibition pattern was confirmed by treating PAD2 or PAD4 with 2CA, and the mixture was incubated for one hour. Then the native enzyme and that treated with 2CA were subjected to tryptic digestion. These peptidic fragments then were subjected to LC/MS/MS analysis to identify any 2CA modified peptide fragments in the drug treated samples, which were contrasted with that from native protein digestion. This fragment analysis led to the identification of the peptide, F$^{850}$ LGEVHC*GTNVR (SEQ ID NO: 1). This peptide sequence corresponds to the active site region of PAD, and additionally Cys656 is the catalytic residue in the active site of PAD2 that is modified by an acetamidine moiety of 2CA confirming the covalent modification of PAD2 with 2CA.[46]

MS Disease Attenuation In Vivo by 2CA in the ND4 Mouse Model.

The relevance of PAD inhibitors to preventing demyelination and potentially for the treatment of MS was investigated in mice using four independent models.[46] The ND4 mouse is a transgenic mouse containing 70 copies of the cDNA for DM20 (a myelin proteolipid protein) which demyelinates spontaneously at 3 months of age. Heterozygous littermates are normal animals from birth until 10-12 weeks of age at which stage they spontaneously develop a non-autoimmune, primary progressive and ultimately fatal CNS demyelinating condition.[49,50] In these mice, disease progression is associated with increased expression of PAD in myelin, and hypercitrullination of myelin protein and histone H3 proteins due to the enhanced levels of PAD.[21,51] Thus, this is a good model to evaluate the effect of drugs on the demyelinating conditions such as MS.

For the in vivo efficacy determination, ND4 mice were administered 2CA (5 mg/kg) i.p. every other day. The drug treatment was initiated either well before disease onset at 2 months of age of the mice or during early stages after disease onset at 3.5 months of age, and mice were observed for a period of 4-5 months after the initiation of the treatment (FIG. 3). Early and prolonged 2CA administration essentially prevented the disease (triangle profile in FIG. 3A). Most untreated mice were sacrificed with severe disease by 6 months of age, while none died in the treatment groups and all mice in the treatment group received the treatment until the end of the study at 6 months. The second group of mice was administered 2CA after the early disease onset at age 3.5 months and they did not show disease progression during the treatment period of up to 6 months of age (FIG. 3B), but a mild disability continued. However, fully progressive clinical disease re-emerged promptly after therapy cessation at 6 months. The above data providing a temporal link between demyelinating disease protection by 2CA and relapse after therapy cessation place PAD-mediated citrullination and disease progression in the executive arm of transgene-driven pathogenesis in this demyelinating disease model.[46]

Overall, it can be concluded from the above experiments that 2CA induced dramatic disease attenuation, but required continued treatment with the drug due to obvious persistence of pathogenic transgene expression.

In further analysis, it was observed that an untreated ND4 transgenic mouse brain exhibited citrullination levels (due to PAD2 and PAD4 activities) higher than those in a normal mouse brain (FIG. 4A, second bar from the left vs. leftmost bar). When PAD activity was observed right after the cessation of 2CA treatment (at 6 months), it was found to be attenuated and was almost equivalent to that observed in a normal mouse brain (FIG. 4A, third bar from the left). Two months after 2CA therapy cessation, however, PAD activity in the white matter of brain was observed to be considerably overshot (and rapid disease progression) (FIG. 4A, rightmost bar). In further analysis, PAD2 gene expression measured by its mRNA levels paralleled citrullination due to PAD activity, suggesting that disease-induced elevations in citrullination of MBP are regulated at the transcriptional level implying the participation of PAD2 (FIG. 4B).

The levels of PAD expression and the corresponding enzymatic activities, hypercitrullination and demyelination were further correlated with the morphological changes in myelin structure by transmission electron microscopy (TEM) of optic nerve cross-sections from the 6 months old mice right after 2CA treatment cessation (FIG. 5). In non-transgenic (normal) ND4 littermates, axons were well myelinated with myelin of uniform thickness (FIG. 5A, left panel). ND4 transgenic mice showed wide areas of myelin loss, and degradation and nude axons were common following development of the disease state after 3 months post-birth (FIG. 5A, middle panel). At 6 months of age, immediately following 2CA treatment, this morphology in ND4 mice was clearly improved, with few axons seriously affected (FIG. 5A, right panel). However, two months after the cessation of 2CA treatment, myelin loss and thinning of the axons reappeared (FIG. 5B). Luxol-fast-blue staining of myelin showed impressive myelin deficits and pronounced vacuolization in PBS-treated ND4 mice, defects which were dramatically improved in 2CA-treated mice.[46] When treatment was ceased, myelinolysis re-emerged indicating disease progression, as indicated above.

To quantify the above myelin changes, G-ratios (axon diameter/fiber diameter) were calculated from ~500 non-contiguous semi-thin sections per treatment group. Compared to healthy littermates (G-ratio 0.74+0.13), ND4 mice showed a reduction in optic nerve myelin thickness: G-ratio 0.96+0.3 (p=0.0013). In 2CA-treated ND4 mice, myelin thickness was slightly improved and showed less variation (G ratio: 0.9+0.15). These treatment data are typical for remyelination, where the original myelin thickness is never re-achieved. These results strongly suggest that 2CA, a PAD inhibitor, showed good efficacy in the ND4 transgenic mice attenuating the hypercitrullination-mediated demyelination, and promoting remyelination.

Disease Attenuation by 2CA in MOG-EAE Mouse Model.

A more commonly used fatal MOG-EAE model was also used to test the efficacy of 2CA and to understand the effects of PAD inhibitors on demyelination. Fatal EAE was induced in C57BL/6 mice with 100 μg of MOG35-55 peptide emulsified in Freund's complete adjuvant and 300 ng of pertussis toxin. At the earliest sign of disease, typically 9 days post-immunization, groups of mice received either PBS or 2CA (5 mg/kg i.p., every other day) (FIG. 6). Untreated mice developed progressive disease rapidly and were sacrificed when moribund around day 19 (FIG. 6B). When treated with 2CA starting day 9, treatment did not affect the disease course until day 14 (when compared to untreated mice, FIG. 6A). After day 14, disease progression halted, and recovery began, leaving ~50% survival by day 30 (FIG. 6B)—a significant outcome in this aggressive model. When 2CA treatment was started before immunization, disease lethality was zero. Despite the severity of disease in this animal model, there was relatively little histopathology in brain. However, vacuolar demyelination and lymphoid infiltration were prominent in the spinal cord of the PBS-treated mice. In the 2CA treatment group, surviving mice showed much improved, virtually normal spinal histology (see ref. 46). Additionally, in a separate study using chronic relapsing EAE model, diseased mice showed significant improvement after receiving 2CA treatment (for details, see ref. 46).

In the 2CA-treated group, some scattered CD3+ T cells were still detected when very sensitive immunostaining was performed on samples from treated animals, but the heavy T cell clusters seen in PBS-treated controls were absent suggesting that when treated with 2CA, the resulting effect may be the suppression of tissue T cell expansion. PAD activities in the brain white matter of PBS-treated mice were elevated, as expected, and 2CA effectively attenuated this elevated PAD activity. In the spinal cord of the EAE animals also, PAD activities of PBS-treated group were 3-fold higher than that in the normal mice, but reductions to normal levels were once again observed following treatment with the PAD inhibitor 2CA. No relapse was observed in the 2CA-treated group.

Additional experiments using pMOG35-55 peptide, additional replacement peptides carrying one or two citrullines in place of one or two Arg residues in the offensive MOG peptide, indicated that the disease-related T cell autoreactivity repertoire prominently includes recognition of citrulline-containing epitopes, an observation with precedence in the literature.[52] This led to the conclusion that the inhibition of PAD activities by 2CA in the early phase of the EAE model produced a major reduction of autoreactive T cell pools.[46] While not wishing to be limited by theory, this could provide a mechanistic explanation for the 2CA-induced failure to generate the massive T cell tissue invasion characteristic of the effector phase of this disease. The remaining infiltrates of scattered CD3+ T cells in treated survivors may be either anergic or non-specific bystanders with little pathogenicity, since there were no relapses after therapy cessation.

Overall, these in-depth studies to understand the effects of 2CA on the spontaneous demyelinating disease (ND4 transgenic mouse) model and the MOG-EAE model indicated a good potential for study of the inhibitors of deiminases to inhibit demyelination. 2CA has no specific structural features that provide specificity to PAD or its isozyme catalytic site. It is a polar molecule due to the acetamidine structure, as well as a reasonably reactive molecule (covalent inhibitor). It has the ability to react with a variety of nucleophiles in vivo causing irreversible modifications (FIG. 2).

Structures of PAD Enzymes.

Structurally, PAD enzymes are $Ca^{2+}$-dependent enzymes that catalyze the conversion of arginine residues in proteins to citrulline via the deimination of the guanidinium moiety in the side chain of Arg residues.[53,54] The structure consists of the N-terminal domain predominately folded into β-sheets, and the C-terminal domain where the catalytic site is located. The catalytic site, where the substrate binds, has two Asp residues, one His residue and a Cys residue that are involved in the deimination reaction. Acidic amino acids, Asp350 and Asp473, function as general base residues during the hydrolysis of the amine in the guanidinium moiety of the peptidyl arginines. These two Asp residues are located in the bottom of the substrate-binding pocket (FIG. 7). 2CA, due to its acetamidine structure carrying a positive charge, binds at this anionic pocket and modifies the Cys residue that is in close proximity (FIG. 2). 2CA does not carry any additional structural features that provide it with specificity to inhibit PAD enzymes only, and not any other similar enzymes.

Over the past decade, there have been only a handful of efforts focused on understanding various ligands, their interactions and the inhibitors targeting PAD enzymes, and most notably, various peptide derivatives to understand the substrate and inhibitor properties targeting PAD enzymes.[39,55,56,57] The most potent non-peptidic compounds from these investigations are chlortetracycline, a tetracycline derivative with an $IC_{50}$ of 100±10 μM as a competitive inhibitor and a substrate analog, F-amidine with an $IC_{50}$ of 21±2.1 μM as an Irreversible inactivator.

SUMMARY OF THE APPLICATION

In vitro enzymology experiments disclosed herein revealed that new and known imidazolidinediones are inhibitors of PAD1, PAD2 and PAD4. A clear improvement in clinical scores was observed in MOG-EAE mice receiving, for example, the compound of Formula (Ia) in comparison to a control group.[58] Analysis of brain samples of these mice revealed that immune response decreased after treatment with the PAD inhibitor of Formula (Ia) as a result of the inhibition of citrullination. Therefore, the compounds of the present application are useful as medicaments, for example, for treating diseases, disorders or conditions characterized by or associated with the hypercitrullination of proteins by peptidyl arginine deiminase (PAD) enzymes such as PAD1, PAD2 and PAD4.

Accordingly, the present application includes a method for treating diseases, disorders or conditions characterized by or associated with the hypercitrullination of proteins by PAD enzymes comprising administering a therapeutically effective amount of one or more compounds of the Formula I:

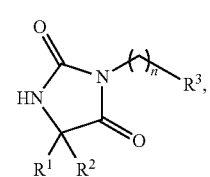

wherein
$R^1$ and $R^2$ are independently selected from $C_{1-6}$alkyl and $C_{1-4}$alkyleneR$^4$; wherein $R^4$ is selected from COOR$^5$, Ph, $C_{3-6}$cycloalkyl and NHR$^6$; wherein $R^5$ is selected from H and $C_{1-6}$alkyl, and $R^6$ is selected from H, Ac and Bz;
$R^3$ is selected from:

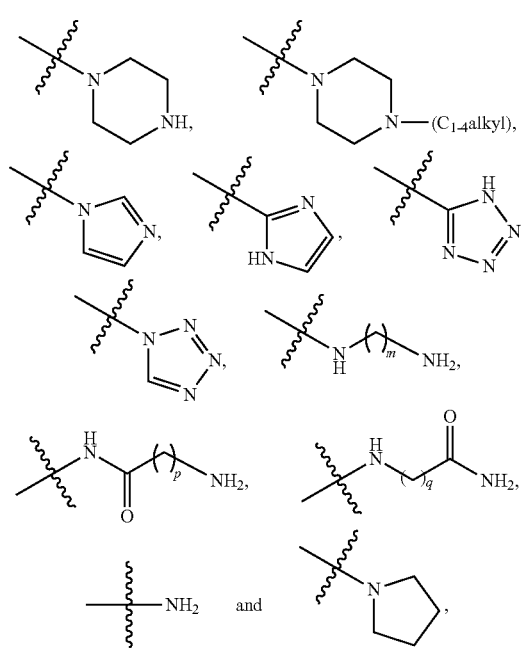

in which any one of the available hydrogen atoms on $R^3$ is optionally substituted with $C_{1-4}$alkyl or cyano; and
m, n, p, and q are, independently, 1, 2 or 3,
or a pharmaceutically acceptable salt or solvate thereof, to a subject in need thereof. Examples of such diseases, disorders or conditions include, for example, multiple sclerosis (MS), rheumatoid arthritis, Alzheimers disease, scrapie, psoriasis and Creutzfeld-Jacob disease.

The present application also includes a compound of the Formula I:

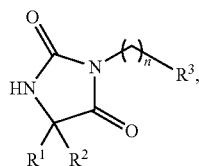

wherein
$R^1$ and $R^2$ are independently selected from $C_{1-6}$alkyl and $C_{1-4}$alkylene$R^4$; wherein $R^4$ is selected from $COOR^5$, Ph, $C_{3-6}$cycloalkyl and $NHR^6$; wherein $R^5$ is selected from H and $C_{1-6}$alkyl, and $R^6$ is selected from H, Ac and Bz; $R^3$ is selected from:

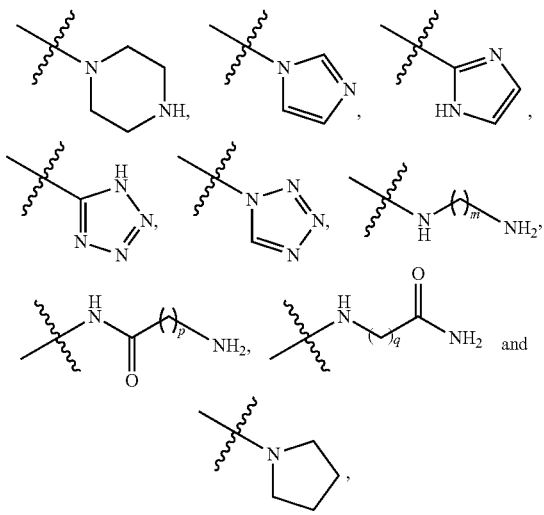

in which any one of the available hydrogen atoms on $R^3$ is optionally substituted with $C_{1-4}$alkyl or cyano; and m, n, p and q are, independently, 1, 2 or 3; except when $R^1$ and $R^2$ are $C_{1-2}$alkyl and $R^3$ is piperazinyl, then n does not equal 1 or 2 and when $R^3$ is pyrrolidinyl, n does not equal 1;
or a pharmaceutically acceptable salt or solvate thereof.

The present application also includes a composition comprising one or more novel compounds of Formula I as described above and a carrier. In an embodiment, the composition is a pharmaceutical composition comprising one or more compounds of Formula I as described above and a pharmaceutically acceptable carrier.

Other features and advantages of the present application will become apparent from the following detailed description. It should be understood, however, that the detailed description and the specific examples while indicating embodiments of the application are given by way of illustration only, the scope of the claims should not be limited by the embodiments set forth in the examples, but should be given the broadest interpretation consistent with the description as a whole.

BRIEF DESCRIPTION OF THE DRAWINGS

The present application will now be described in greater detail with reference to the drawings in which.

DETAILED DESCRIPTION OF THE APPLICATION

I. Definitions

Figure 1:
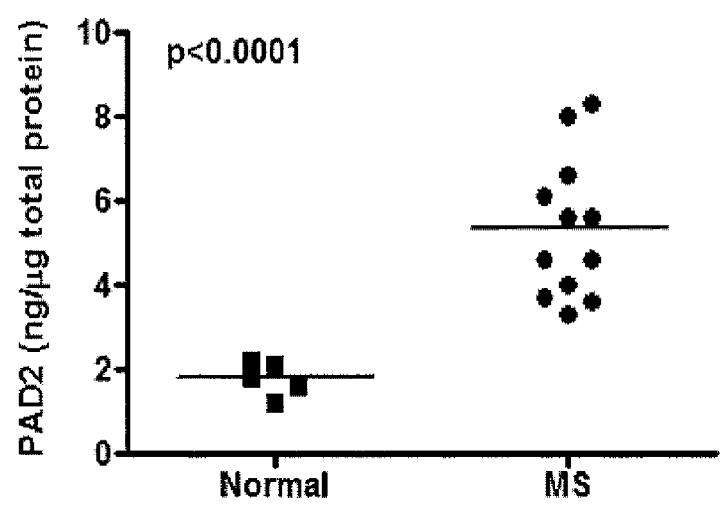
FIG. 1 shows (A) levels of PAD2 protein in white matter from normal and MS human brain by immunoblot (n≥5, p<0.0001); (B) citrullinated protein in white matter of the brain tissue of normal and MS patients, measured from immunoslot blot as pixel density (n≥4, p<0.01); (C) PAD enzyme activity (i.e. PAD2 and PAD4) in normal and MS tissue, with or without preincubation with 2CA (n≥5, p<0.05).[46]
Figure 1:
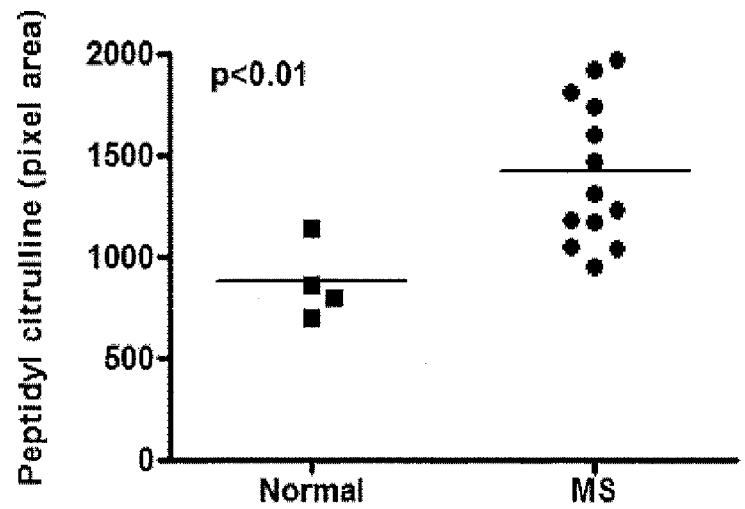
Figure 1:
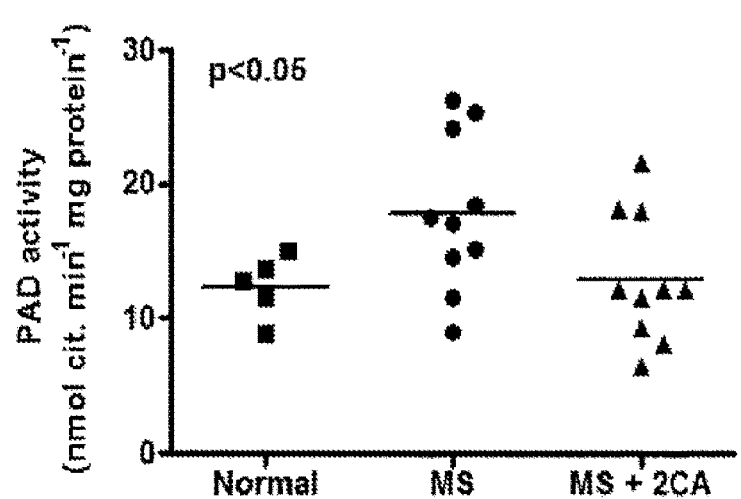
Figure 2:
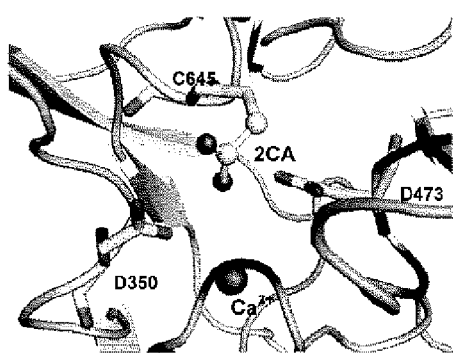
FIG. 2 shows a model of the covalent complex of 2CA bound to Cys645 in the active site of PAD4. The sphere labeled $Ca^{2+}$ is one of the $Ca^{2+}$ ions in proximity to the active site.
Figure 3:
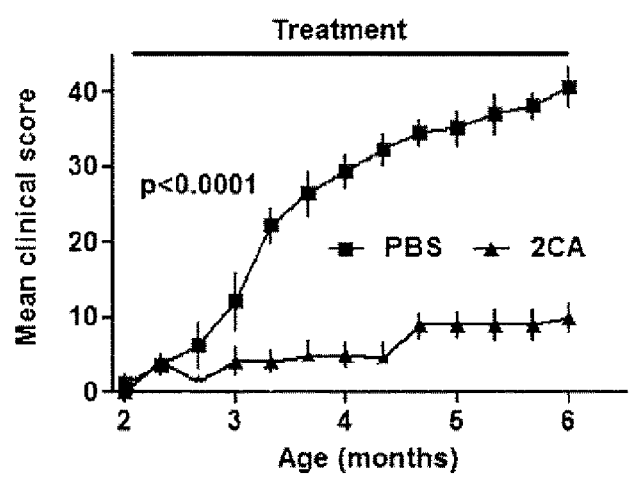
FIG. 3 shows attenuating effects of the treatment with non-specific PAD inhibitor 2CA on the demyelinating disease in ND4 mice. (A) ND4 mice were treated with PBS or 2CA (5 mg/kg) starting at 2 months of age well before disease onset (n=5, p<0.0001). (B) ND4 mice treated at disease onset at 3.5 months of age either with PBS or with 2CA, and the treatment was stopped at the age of 6 months (n≥4, p<0.0001).
Figure 3:
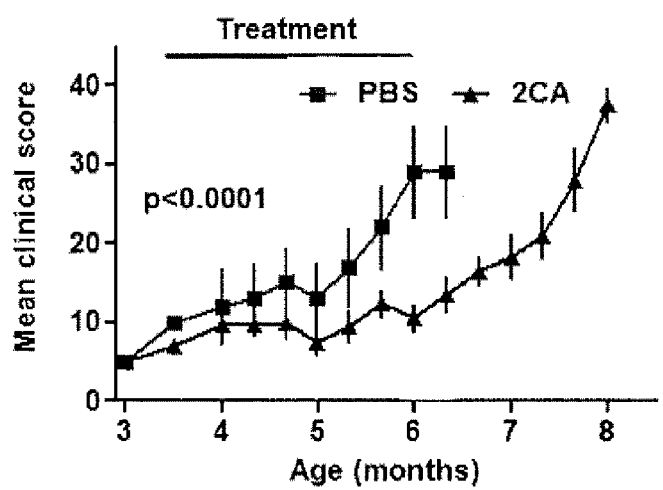
Figure 4:
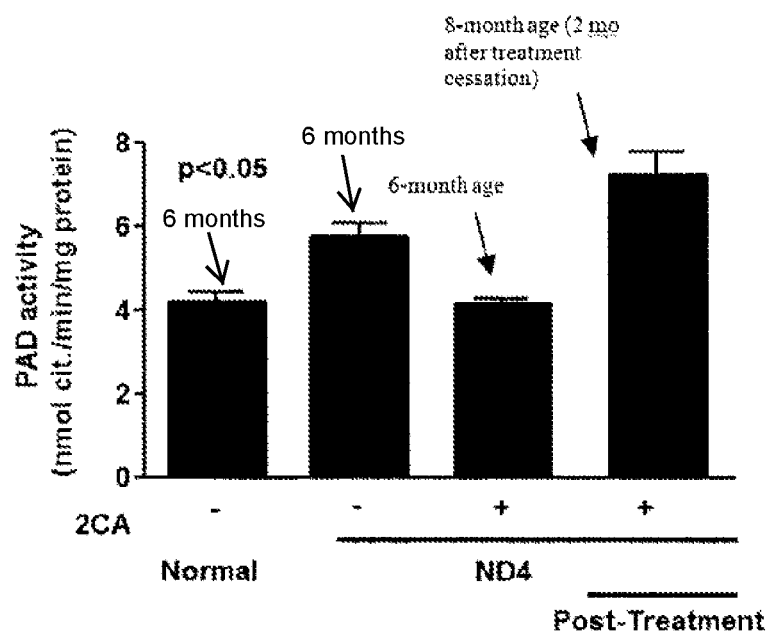
FIG. 4 shows (A) citrullination (PAD2 and PAD4 activities) in brain extracts of ND4 transgenic mice after treatment with 2CA beginning at the early onset stage of the disease at 3.5 months, and continuing treatment up to 6 months age (n≥5, p<0.05). PAD activity was evaluated right after the termination of the treatment at age 6 months ($3^{rd}$ bar), and two months after discontinuation of the treatment, at age 8 months ($4^{th}$ bar); (B) PAD2 RT-PCR in individual white matter extracts of normal, PBS- and 2CA-treated ND4 mice (n=9, p<0.05).
Figure 4:
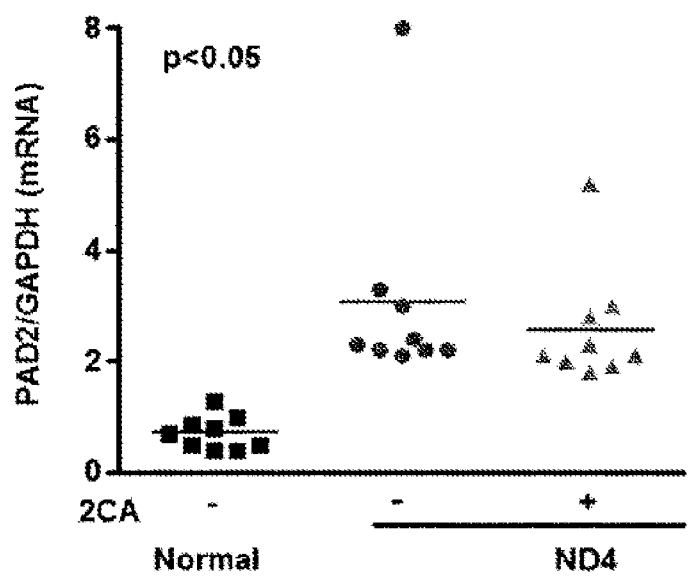
Figure 5:
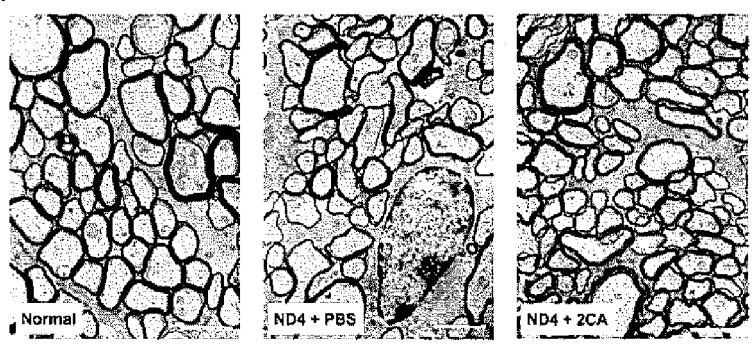
FIG. 5 shows (A) exemplary transmission electron microscopy (TEM) micrographs of the optic nerve sections from normal, PBS, and 2CA-treated ND4 mice (left, middle and right panels, respectively) at 6 months of age (bar 2 μm); (B) an exemplary TEM micrograph of optic nerve sections from 2CA-treated ND4 mice, 2 months after treatment cessation (bar 2 μm).
Figure 5:
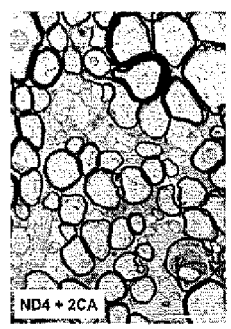
Figure 6:
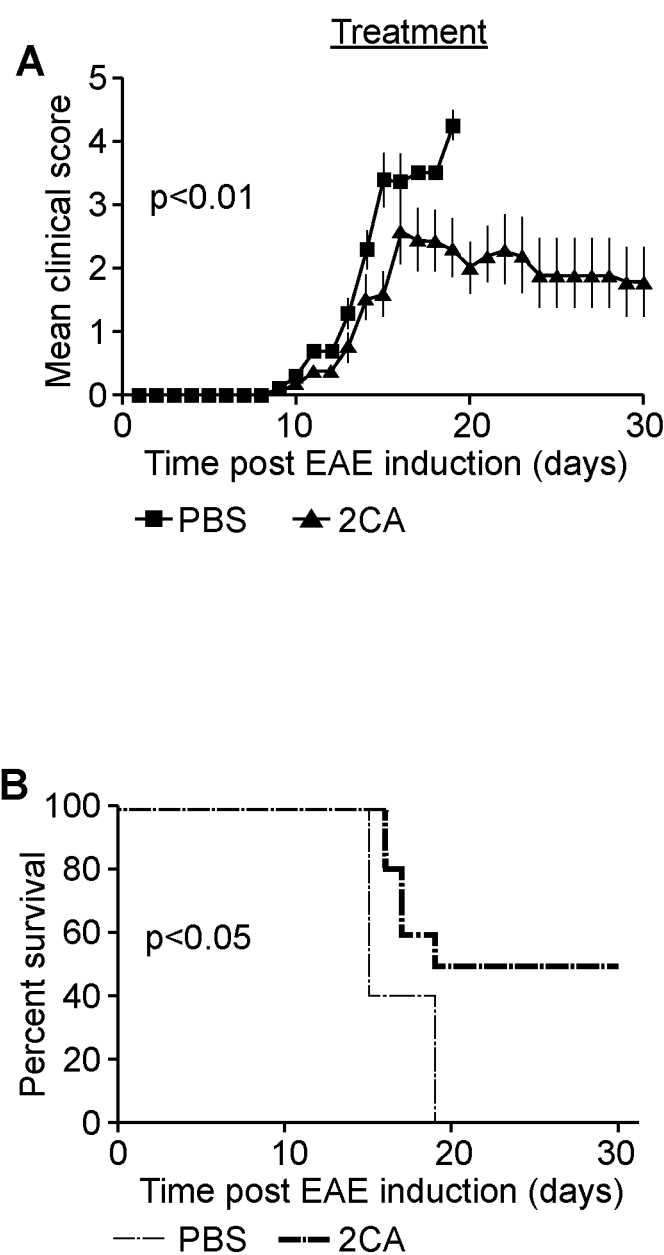
FIG. 6 shows (A) the clinical progression (n≥5, p<0.0001) and (B) survival (n≥5, p<0.01) during acute MOG-EAE in C57BL/16 mice treated with PBS or 2CA.
Figure 7:
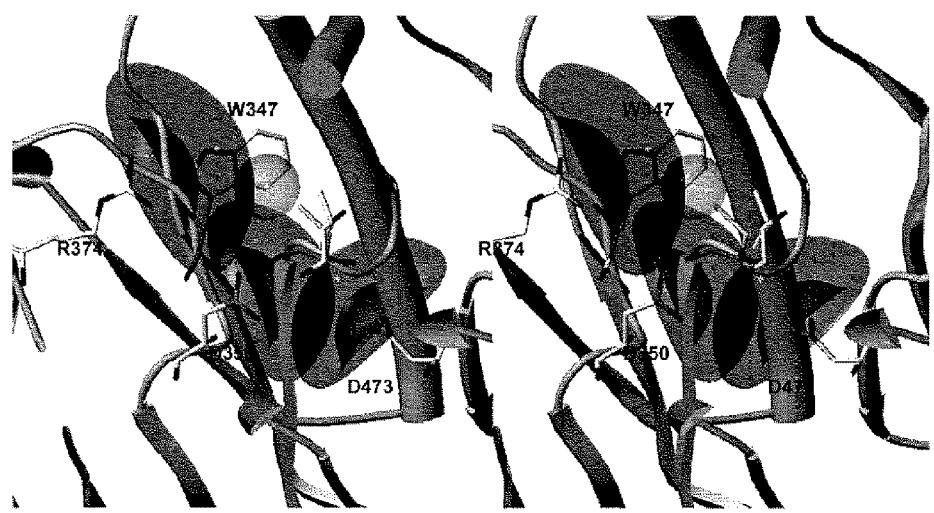
FIG. 7 shows a stereo view of the four selected features in the catalytic site of PAD4 overlapped onto the enzyme (cartoon model; source: crystal structure of PAD4 bound by a substrate analog N-benzoyl ethyl ester-L-arginine amide, PDB code: 1WDA)

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 50, 55, 60, 65, 70, 75, 80, 85, 90, 95 or 100% of the starting material or substrate is converted to product.

The term "suitable", as in for example, "suitable reagents", "suitable conditions", "suitable solvent" or "suitable amount" means that the selection of a particular compound, group or conditions would depend on the specific synthetic manipulation to be performed, and the identity of the molecule to be transformed, but the selection would be well within the skill of a person trained in the art. All process steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOime, J. F. W. Ed., Plenum Press, 1973, in Greene, T. W. and Wuts, P. G. M., "Protective Groups in Organic Synthesis", John Wiley & Sons, $3^d$ Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, benzoyl, dimethoxytrityl, methoxyethoxymethyl ether, methoxymethyl ether, pivaloyl, p-methoxybenzyl ether, tetrahydropyranyl, trityl, ethoxyethyl ethers, carbobenzyloxy, benzoyl and the like.

The term "compound(s) of the application" or "compound(s) of the present application" and the like as used herein includes compounds of Formula I, and a pharmaceutically acceptable salt and/or solvate thereof as defined herein.

The term "subject" as used herein includes all members of the animal kingdom including mammals, and suitably refers to humans.

The term "pharmaceutically acceptable" means compatible with the treatment of subjects, in particular humans.

The term "pharmaceutically acceptable salt" means an acid addition salt or a base addition salt which is suitable for, or compatible with, the treatment of subjects.

An acid addition salt which is suitable for, or compatible with, the treatment of subjects as used herein means any non-toxic organic or inorganic salt of any basic compound. Basic compounds that form an acid addition salt include, for example, compounds comprising an amine group. Illustrative inorganic acids which form suitable salts include hydrochloric, hydrotrifluoroacetic, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art. In an embodiment, the acid addition salt is a hydrochloride or hydrotrifluoroacetic acid salt.

A base addition salt which is suitable for, or compatible with, the treatment of subjects as used herein means any non-toxic organic or inorganic base addition salt of any acidic compound. Acidic compounds that form a base addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

In embodiments of the application, the compounds described herein have at least one asymmetric centre. Where compounds possess more than one asymmetric centre, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early MS can be treated to prevent progression, or alternatively a subject in remission can be treated with a compound or composition described herein to prevent recurrence. Treatment methods comprise administering to a subject a therapeutically effective amount of one or more of the compounds of the application and optionally, consists of a single administration, or alternatively comprises a series of administrations. For example, the compounds of the application may be administered at least once a week. However, in another embodiment, the compounds may be administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, the age of the patient, the concentration, the activity of the compounds of the application, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required. For example, the compounds are administered to the subject in an amount and for a duration sufficient to treat the patient.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition characterized by or associated with the hypercitrullination of proteins by PAD enzymes or manifesting a symptom associated with a disease, disorder or condition characterized by or associated with the hypercitrullination of proteins by PAD enzymes.

As used herein, the term "effective amount" or "therapeutically effective amount" means an amount effective, at dosages and for periods of time necessary to achieve the desired result. For example, in the context of treating a disease, disorder or condition characterized by or associated with the hypercitrullination of proteins by peptidyl arginine deiminase (PAD) enzymes, an effective amount is an amount that, for example, reduces the hypercitrullination of proteins compared to the hypercitrullination of proteins without administration of the compound. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

The terms "characterized by" or "associated with" as used herein refers to a disease, disorder or condition in a subject wherein at least one of the causes is an enhanced level of activity in one or more of the PAD enzymes that catalyze the post-translational citrullination of proteins, compared to subjects that do not have the disease, disorder or condition. In an embodiment, PAD enzyme is PAD1, PAD2, PAD3, PAD4 and/or PAD6. In a further embodiment, the PAD enzyme is PAD1, PAD2 and/or PAD4. In yet another embodiment, the PAD enzyme is PAD2 and/or PAD4.

The term "administered" as used herein means administration of a therapeutically effective dose of a compound or composition of the application to a cell either in cell culture or in a patient.

The term "alkyl" as used herein, whether it is used alone or as part of another group, means straight or branched chain, saturated alkyl groups. The term $C_{1-6}$alkyl means an alkyl group having 1, 2, 3, 4, 5 or 6 carbon atoms.

The term "alkylene" as used herein, whether alone or as part of another group, means an alkyl group that is bivalent; i.e. that is substituted on two ends with another group.

The term "cycloalkyl" as used herein, whether it is used alone or as part of another group, means cyclic, saturated alkyl groups. The term $C_{3-6}$cycloalkyl means a cycloalkyl group having 3, 4, 5 or 6 carbon atoms.

The term "optionally substituted" as used herein means that the referenced group or atom is unsubstituted or substituted with another (different) group.

The term "available hydrogen atoms" as used herein refers to hydrogen atoms on a molecule that can be replaced with another group under conditions that will not degrade or decompose the parent compound. Such conditions include the use of protecting groups to protect sensitive functional groups in the molecule while the hydrogen atom is being replaced.

2CA as used herein refers to 2-Cl-acetamidine:

Ac as used herein refers to the group acetyl.
Bz as used herein refers to the group benzoyl.
Ph as used herein refers to the group phenyl.
t-Boc as used herein refers to the group t-butyloxycarbonyl.
Ts (tosyl) as used herein refers to the group p-toluenesulfonyl
Ms as used herein refers to the group methanesulfonyl
TBDMS as used herein refers to the group t-butyldimethylsilyl.
TBDPS as used herein refers to the group t-butyldiphenylsilyl.
TMS as used herein refers to the group trimethylsilyl.
Tf as used herein refers to the group trifluoromethanesulfonyl.
Ns as used herein refers to the group naphthalene sulphonyl.
Bn as used herein refers to the group benzyl.
Fmoc as used here refers to the group fluorenylmethoxycarbonyl.
The term "piperazinyl" as used herein refers to the group:

The term "pyrrolindyl" as used herein refers to the group:

II. Methods and Uses of the Application

As noted above, in vitro enzymology experiments disclosed herein revealed that new and known imidazolidinediones are inhibitors of PAD1, PAD2 and PAD4. A clear improvement in clinical scores was observed in MOG-EAE mice receiving the compound of Formula (Ia) in comparison to a control group. Analysis of brain samples of these mice revealed that immune response decreased after treatment with the PAD inhibitor of Formula (Ia) as a result of the inhibition of citrullination. Therefore, the compounds of the present application are useful for treating diseases, disorders or conditions characterized by or associated with the hypercitrullination of proteins by peptidyl arginine deiminase (PAD) enzymes.

Accordingly, the present application includes a method for treating diseases, disorders or conditions characterized by or associated with the hypercitrullination of proteins by PAD enzymes comprising administering a therapeutically effective amount of one or more of the compounds of the Formula I:

wherein
$R^1$ and $R^2$ are independently selected from $C_{1-6}$ alkyl and $C_{1-4}$ alkylene$R^4$; wherein $R^4$ is selected from COOR$^5$, Ph, $C_{3-6}$cycloalkyl and NHR$^6$; wherein $R^5$ is selected from H and $C_{1-6}$ alkyl, and $R^6$ is selected from H, Ac and Bz;
$R^3$ is selected from:

in which any one of the available hydrogen atoms on $R^3$ is optionally substituted with $C_{1-4}$alkyl or cyano; and
m, n, p, and q are, independently, 1, 2 or 3,
or a pharmaceutically acceptable salt or solvate thereof, to a subject in need thereof.

The application also includes a use of a compound of Formula I:

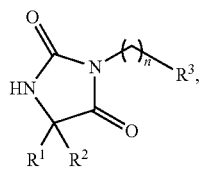

wherein
$R^1$ and $R^2$ are independently selected from $C_{1-6}$alkyl and $C_{1-4}$alkylene$R^4$; wherein $R^4$ is selected from COO$R^5$, Ph, $C_{3-6}$cycloalkyl and NH$R^6$; wherein $R^5$ is selected from H and $C_{1-6}$alkyl, and $R^6$ is selected from H, Ac and Bz;
$R^3$ is selected from:

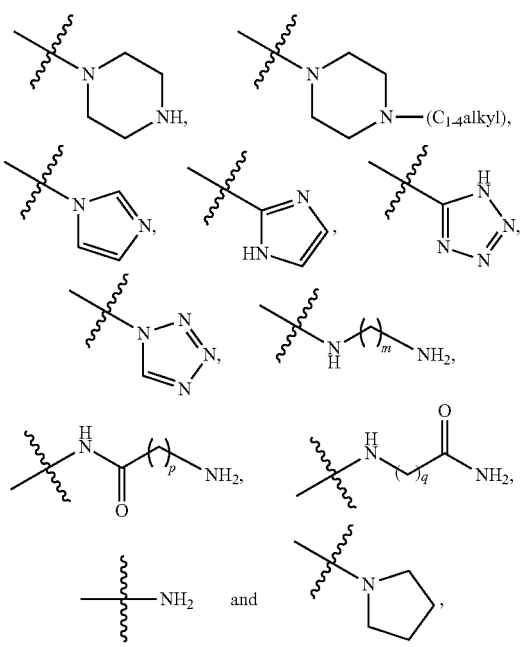

in which any one of the available hydrogen atoms on $R^3$ is optionally substituted with $C_{1-4}$alkyl or cyano; and
m, n, p, and q are, independently, 1, 2 or 3,
or a pharmaceutically acceptable salt or solvate thereof, for treating diseases, disorders or conditions characterized by or associated with the hypercitrullination of proteins by PAD enzymes.

The application further includes a use of a compound of Formula I:

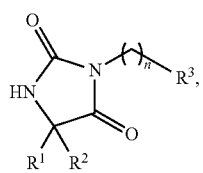

wherein
$R^1$ and $R^2$ are independently selected from $C_{1-6}$alkyl and $C_{1-4}$alkylene$R^4$; wherein $R^4$ is selected from COO$R^5$, Ph, $C_{3-6}$cycloalkyl and NH$R^6$; wherein $R^5$ is selected from H and $C_{1-6}$alkyl, and $R^6$ is selected from H, Ac and Bz;
$R^3$ is selected from:

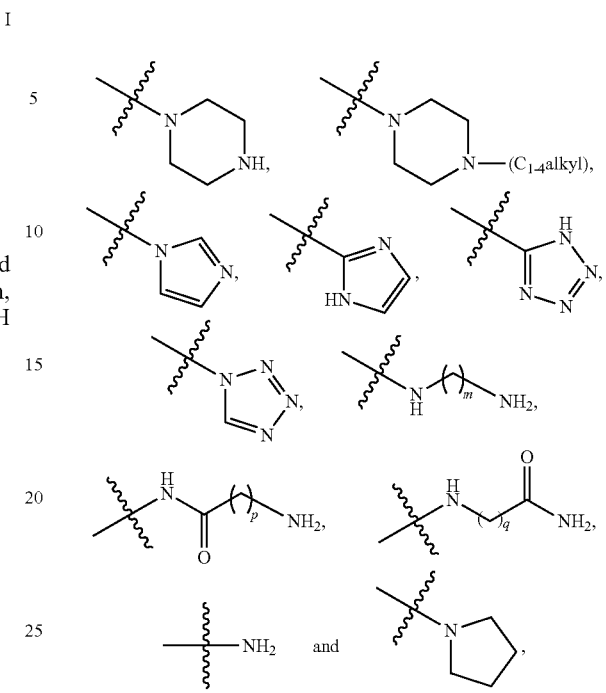

in which any one of the available hydrogen atoms on $R^3$ is optionally substituted with $C_{1-4}$alkyl or cyano; and
m, n, p, and q are, independently, 1, 2 or 3,
or a pharmaceutically acceptable salt or solvate thereof, for the preparation of a medicament for treating diseases, disorders or conditions characterized by or associated with the hypercitrullination of proteins by PAD enzymes.

The application still further includes a compound of Formula I

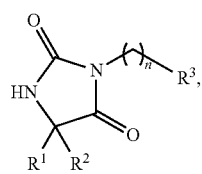

wherein
$R^1$ and $R^2$ are independently selected from $C_{1-6}$alkyl and $C_{1-4}$alkylene$R^4$; wherein $R^4$ is selected from COO$R^5$, Ph, $C_{3-6}$cycloalkyl and NH$R^6$; wherein $R^5$ is selected from H and $C_{1-6}$alkyl, and $R^6$ is selected from H, Ac and Bz;
$R^3$ is selected from:

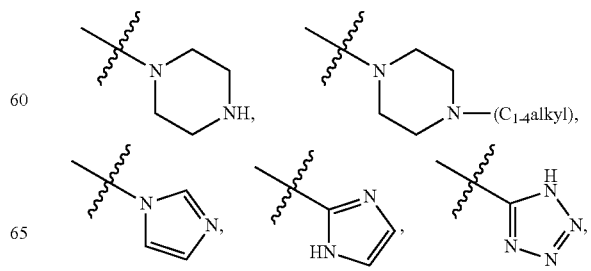

-continued

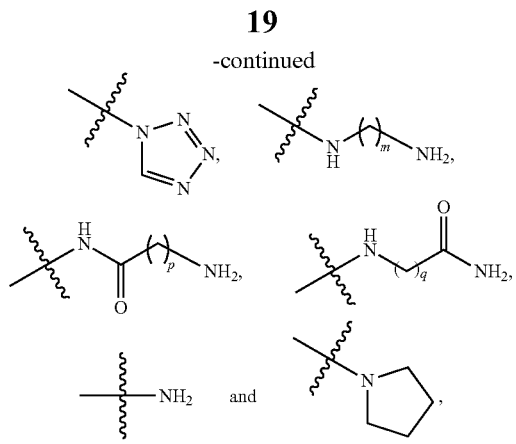

in which any one of the available hydrogen atoms on $R^3$ is optionally substituted with $C_{1-4}$alkyl or cyano; and m, n, p, and q are, independently, 1, 2 or 3, or a pharmaceutically acceptable salt or solvate thereof, for use in treating diseases, disorders or conditions characterized by or associated with the hypercitrullination of proteins by PAD enzymes.

The application yet further includes a compound of Formula I:

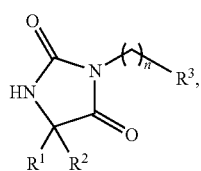

wherein $R^1$ and $R^2$ are independently selected from $C_{1-6}$alkyl and $C_{1-4}$alkylene$R^4$; wherein $R^4$ is selected from COOR$^5$, Ph, $C_{3-6}$cycloalkyl and NHR$^6$; wherein $R^5$ is selected from H and $C_{1-6}$alkyl, and $R^6$ is selected from H, Ac and Bz;

$R^3$ is selected from:

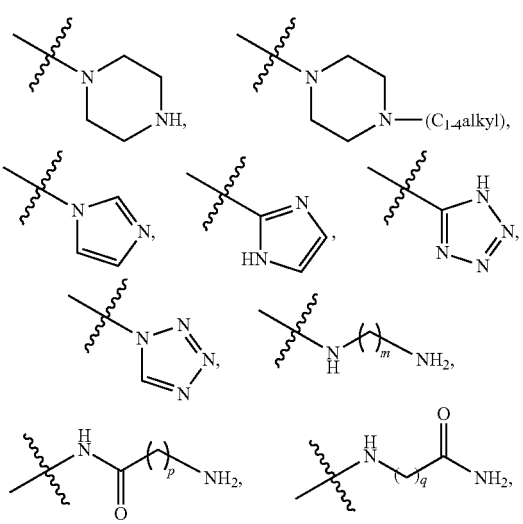

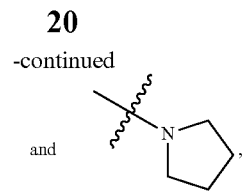

in which any one of the available hydrogen atoms on $R^3$ is optionally substituted with $C_{1-4}$alkyl or cyano; and m, n, p, and q are, independently, 1, 2 or 3, or a pharmaceutically acceptable salt or solvate thereof, for use as a medicament.

In embodiments of the application, $R^1$ and $R^2$ in the compounds of Formula I are independently $C_{1-6}$alkyl. It is a further embodiment that $R^1$ and $R^2$ are independently selected from methyl, ethyl, isopropyl, tert-butyl and iso-pentyl.

In another embodiment of the application, $R^1$ and $R^2$ in the compounds of Formula I are independently $C_{1-4}$alkylene$R^4$; wherein $R^4$ is selected from COOR$^5$, Ph, $C_{3-6}$cycloalkyl and NHR$^6$; wherein $R^5$ is selected from H and $C_{1-6}$alkyl, and $R^6$ is selected from H, Ac and Bz. It is a further embodiment that $R^1$ and $R^2$ are independently selected from $CH_2COOC_2H_5$, $CH_2COOtBu$, $CH_2CH_2COOH$, $CH_2CH_2CH_2COOH$, $CH_2Ph$, $CH_2CH_2Ph$, $CH_2$-cyclohexyl, $CH_2CH_2NH_2$, $CH_2CH_2CH_2NH_2$, $CH_2CH_2NHAc$, $CH_2CH_2NHBz$, $CH_2CH_2CH_2NHAc$ and $CH_2CH_2CH_2NHBz$.

In an embodiment, any one of the available hydrogen atoms on one of the heterocyclic groups of $R^3$ is optionally substituted with $C_{1-4}$alkyl or cyano.

In an embodiment, $R^3$ in the compounds of Formula I is selected from:

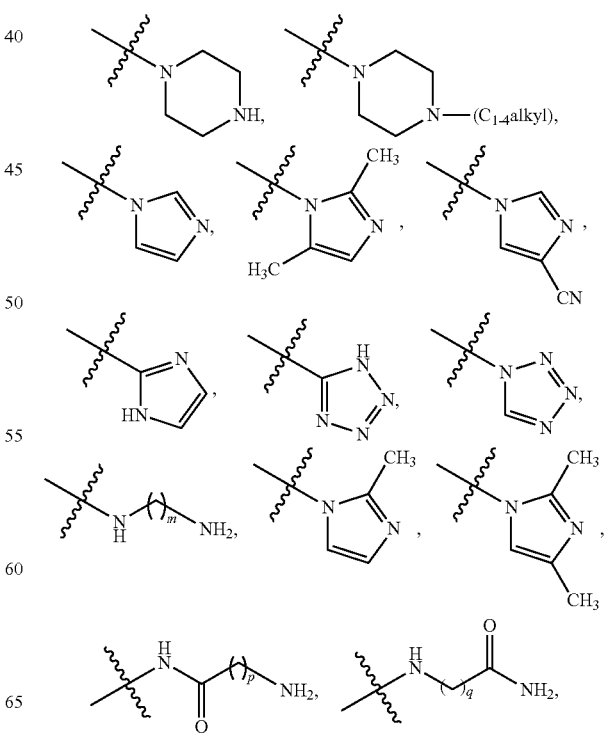

-continued

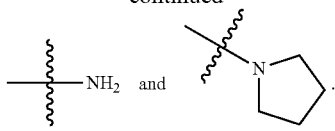

In another embodiment of the application, $R^3$ in the compounds of Formula I is piperazinyl.

In another embodiment, $R^3$ in the compounds of Formula I is

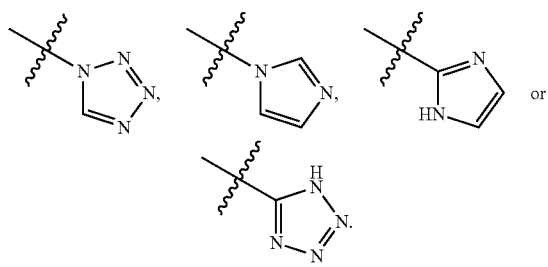

In another embodiment, $R^3$ in the compounds of Formula I is

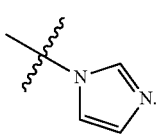 [SMILES: *n1ccnc1]

In another embodiment. $R^3$ in the compounds of Formula I is

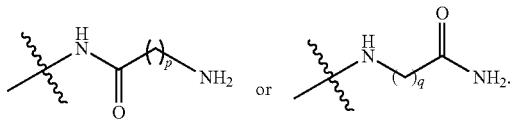

In another embodiment, n in the compounds of Formula I is 1 or 2.

In another embodiment, m in the compounds of Formula I is 1 or 2.

In another embodiment, p and q in the compounds of Formula I is 1.

It is an embodiment of the methods and uses of the application, that the compound of Formula I is selected from a compound of Formula (Ia), Formula (Ib) and Formula (Ic):

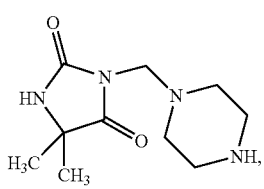

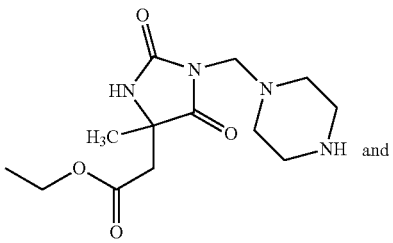

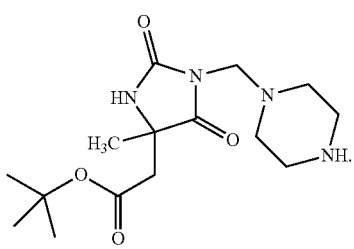

It is an embodiment of the methods and uses of the application, that the compound of Formula I is selected from a compound of Formula (Ig) and Formula (Ih):

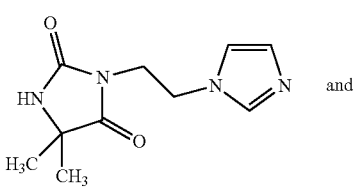

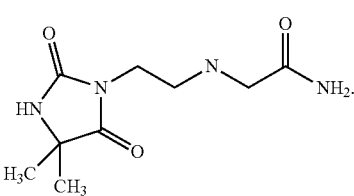

It is a further embodiment of the methods and uses of the application that the compound of Formula I is the compound of Formula (Ia).

In a further embodiment, the compounds of Formula I are acid addition salts. In a further embodiment, the acid salt is a trifluoroacetic acid salt. In another embodiment, the acid salt is a hydrochloric acid salt.

In embodiments of the application, the diseases, disorders or conditions characterized by or associated with the hyper-citrullination of proteins by PAD enzymes such as PAD1, PAD2 and PAD4 include, for example, multiple sclerosis (MS), rheumatoid arthritis, Alzheimer's disease, scrapie, psoriasis and Creutzfeld-Jacob disease. It is an embodiment that the disease, disorder or condition is multiple sclerosis.

In embodiments of the application, the PAD enzyme is PAD1, PAD2 and/or PAD4. In another embodiment of the application, the PAD enzyme is PAD2 and/or PAD4. In another embodiment of the application, the PAD enzyme is PAD2. In a further embodiment of the application, the PAD enzyme is PAD4.

III. Compositions of the Application

The present application also includes a composition comprising one or more compounds of Formula I:

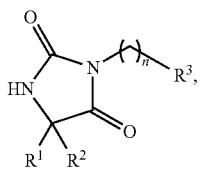

wherein
R[1] and R[2] are independently selected from $C_{1-6}$alkyl and $C_{1-4}$alkyleneR[4]; wherein R[4] is selected from COOR[5], Ph, $C_{3-6}$cycloalkyl and NHR[6]; wherein R[5] is selected from H and $C_{1-6}$alkyl, and R[6] is selected from H, Ac and Bz; R[3] is selected from:
R[3] is selected from:

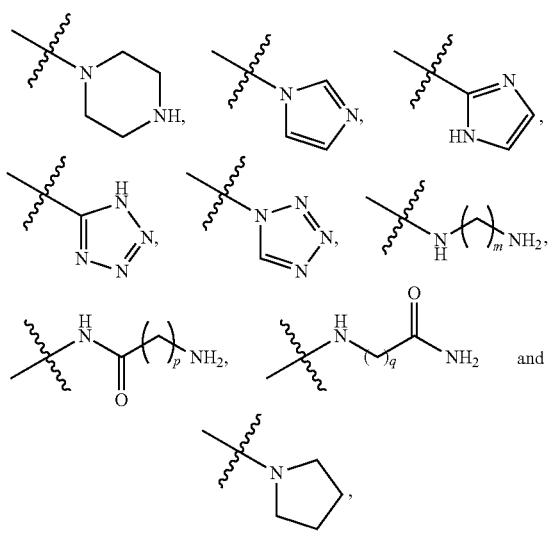

in which any one of the available hydrogen atoms on R[3] is optionally substituted with $C_{1-4}$alkyl or cyano; and
m, n, p and q are, independently, 1, 2 or 3;
except when R[1] and R[2] are $C_{1-2}$alkyl and R[3] is piperazinyl, then n does not equal 1 or 2 and when R[3] is pyrrolidinyl, n does not equal 1;
or a pharmaceutically acceptable salt or solvate thereof, and a carrier.

Said compounds of Formula I are suitably formulated into pharmaceutical compositions for administration to subjects in a biologically compatible form suitable for administration in vivo. Accordingly, the present application further includes a pharmaceutical composition comprising one or more compounds of said compounds of Formula I:
wherein
R[1] and R[2] are independently selected from $C_{1-6}$alkyl and $C_{1-4}$alkyleneR[4]; wherein R[4] is selected from COOR[5], Ph, $C_{3-6}$cycloalkyl and NHR[6]; wherein R[5] is selected from H and $C_{1-6}$alkyl, and R[6] is selected from H, Ac and Bz;
R[3] is selected from:

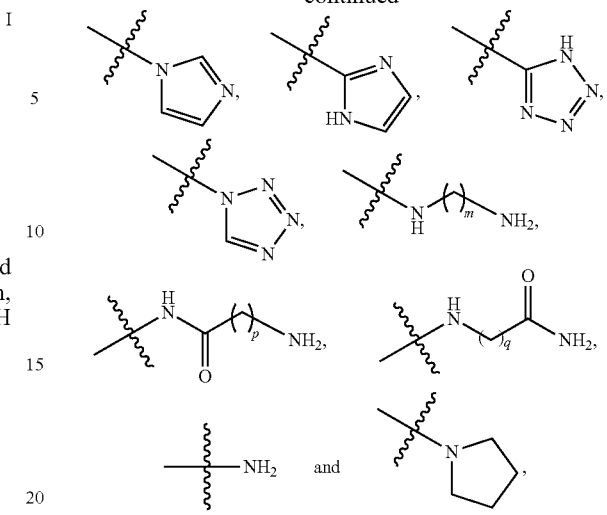

in which any one of the available hydrogen atoms on R[3] is optionally substituted with $C_{1-4}$alkyl or cyano; and
m, n, p, and q are, independently, 1, 2 or 3,
or a pharmaceutically acceptable salt or solvate thereof, and a pharmaceutically acceptable carrier.

In embodiments of the application, R[1] and R[2] in the compounds of Formula I are independently $C_{1-6}$alkyl. It is a further embodiment that R[1] and R[2] are independently selected from methyl, ethyl, isopropyl, tert-butyl and iso-pentyl.

In another embodiment of the application, R[1] and R[2] in the compounds of Formula I are independently $C_{1-4}$alkyleneR[4]; wherein R[4] is selected from COOR[5], Ph, $C_{3-6}$cycloalkyl and NHR[6]; wherein R[5] is selected from H and $C_{1-6}$alkyl, and R[6] is selected from H, Ac and Bz. It is an embodiment that R[1] and R[2] are independently selected from $CH_2COOC_2H_5$, $CH_2COOtBu$, $CH_2CH_2COOH$, $CH_2CH_2CH_2COOH$, $CH_2Ph$, $CH_2CH_2Ph$, $CH_2$-cyclohexyl, $CH_2CH_2NH_2$, $CH_2CH_2CH_2NH_2$, $CH_2CH_2NHAc$, $CH_2CH_2NHBz$, $CH_2CH_2CH_2NHAc$ and $CH_2CH_2CH_2NHBz$.

In an embodiment, any one of the available hydrogen atoms on one of the heterocyclic groups of R[3] is optionally substituted with $C_{1-4}$alkyl or cyano.

In an embodiment, R[3] in the compounds of Formula I is selected from:

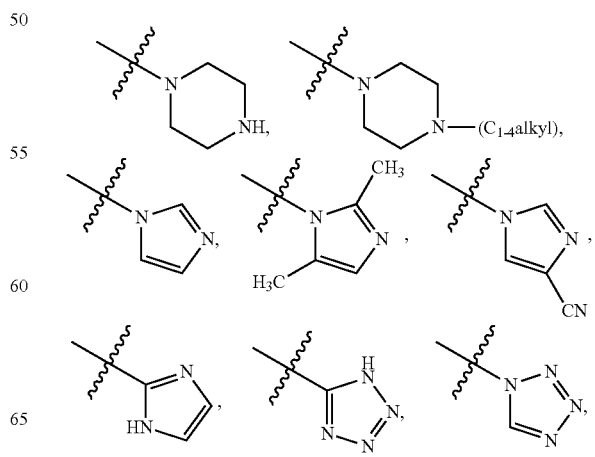

-continued

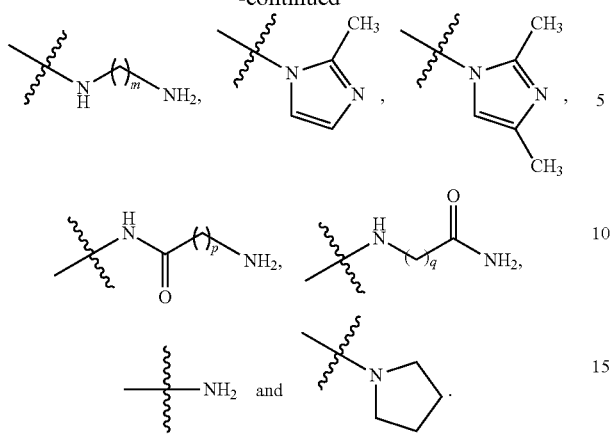

In yet another embodiment of the application, R³ in the compounds of Formula I is piperazinyl.

In another embodiment, R³ in the compounds of Formula I is

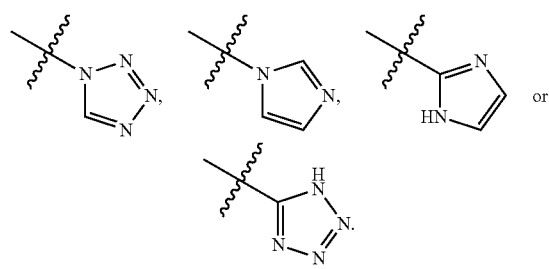

or

In another embodiment, R³ in the compounds of Formula I is

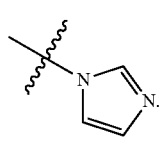 [SMILES: *n1ccnc1]

In another embodiment, R³ in the compounds of Formula I is

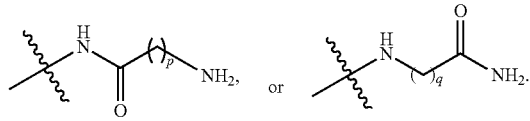

In another embodiment, n in the compounds of Formula I is 1 or 2.

In another embodiment, m in the compounds of Formula I is 1 or 2.

In another embodiment, p and q in the compounds of Formula I is 1.

In a further embodiment of the application, the compound of Formula I is a compound of Formula (Ib):

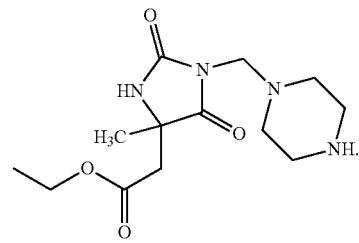

In yet a further embodiment of the application, the compound of Formula I is a compound of Formula (Ic):

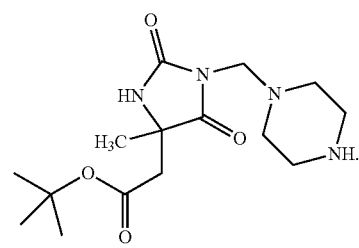

In yet a further embodiment of the application, the compound of Formula I is a compound of Formula (Ig):

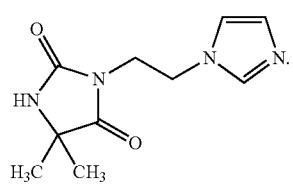

In yet a further embodiment of the application, the compound of Formula I is a compound of Formula (Ih):

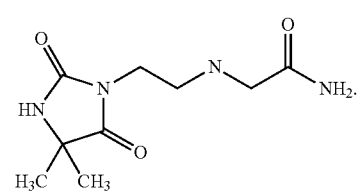

In a further embodiment, the compound of Formula I is an acid addition salts. In a further embodiment, the acid salt is a trifluoroacetic acid salt. In another embodiment, the acid salt is a hydrochloric acid salt.

The compounds of the application may be formulated for administration to a subject in a variety of forms depending on the selected route of administration, as will be understood by those skilled in the art. A compound of the application may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

A compound of the application may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines.

It is also possible to freeze-dry the compounds of the application and use the lyophilizates obtained, for example, for the preparation of products for injection.

A compound of the application may also be administered parenterally. Solutions of a compound of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersion and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compounds of the application may also be delivered by the use of monoclonal antibodies as individual carriers to which the compound molecules are coupled. Compounds of the application may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Compounds of the application may be used alone or in combination with other known agents useful for treating diseases, disorders or conditions characterized by or associated with the hypercitrullination of proteins by PAD enzymes such as PAD2 and PAD4. When used in combination with other agents useful in treating diseases, disorders or conditions characterized by or associated with the hypercitrullination of proteins by PAD enzymes such as PAD2 and PAD4, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The dosage of compounds of the application can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. In an embodiment of the application, compositions formulated for oral administration and the compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. Compounds of the application may be administered in a single daily dose or the total daily dose may be divided into two, three or four daily doses.

IV. Compounds of the Application

Novel imidazolidinediones showing inhibition of PAD1, PAD2 and PAD4 have been prepared.

Accordingly, the present application includes a compound of the Formula I:

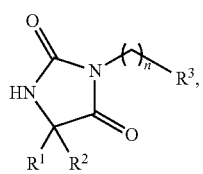

wherein
$R^1$ and $R^2$ are independently selected from $C_{1-6}$alkyl and $C_{1-4}$alkylene$R^4$; wherein $R^4$ is selected from $COOR^5$, Ph, $C_{3-6}$cycloalkyl and $NHR^6$; wherein $R^5$ is selected from H and $C_{1-6}$alkyl, and $R^6$ is selected from H, Ac and Bz;
$R^3$ is selected from:

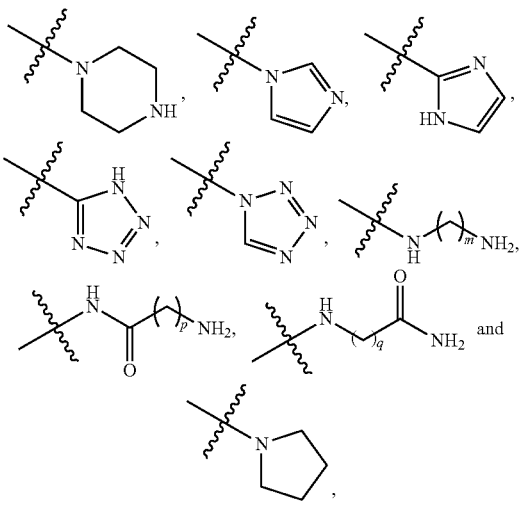

in which any one of the available hydrogen atoms on $R^3$ is optionally substituted with $C_{1-4}$alkyl or cyano; and
m, n, p and q are, independently, 1, 2 or 3;
except when $R^1$ and $R^2$ are $C_{1-2}$alkyl and $R^3$ is piperazinyl, then n does not equal 1 or 2 and when $R^3$ is pyrrolidinyl, n does not equal 1; or a pharmaceutically acceptable salt or solvate thereof.

In embodiments of the application, $R^1$ and $R^2$ are independently $C_{1-6}$alkyl. It is a further embodiment that $R^1$ and $R^2$ are independently selected from methyl, ethyl, isopropyl, tert-butyl and isopentyl.

In another embodiment of the application, $R^1$ and $R^2$ are independently $C_{1-4}$alkylene$R^4$; wherein $R^4$ is selected from $COOR^5$, Ph, $C_{3-6}$cycloalkyl and $NHR^6$; wherein $R^5$ is selected from H and $C_{1-6}$alkyl, and $R^6$ is selected from H, Ac and Bz. It is an embodiment that $R^1$ and $R^2$ are independently selected from $CH_2COOC_2H_5$, $CH_2COOtBu$, $CH_2CH_2COOH$, $CH_2CH_2CH_2COOH$, $CH_2Ph$, $CH_2CH_2Ph$, $CH_2$-cyclohexyl, $CH_2CH_2NH_2$, $CH_2CH_2CH_2NH_2$, $CH_2CH_2NHAc$, $CH_2CH_2NHBz$, $CH_2CH_2CH_2NHAc$ and $CH_2CH_2CH_2NHBz$.

In an embodiment, any one of the available hydrogen atoms on one of the heterocyclic groups of $R^3$ is optionally substituted with $C_{1-4}$alkyl or cyano.

In an embodiment, $R^3$ in the compounds of Formula I is selected from:

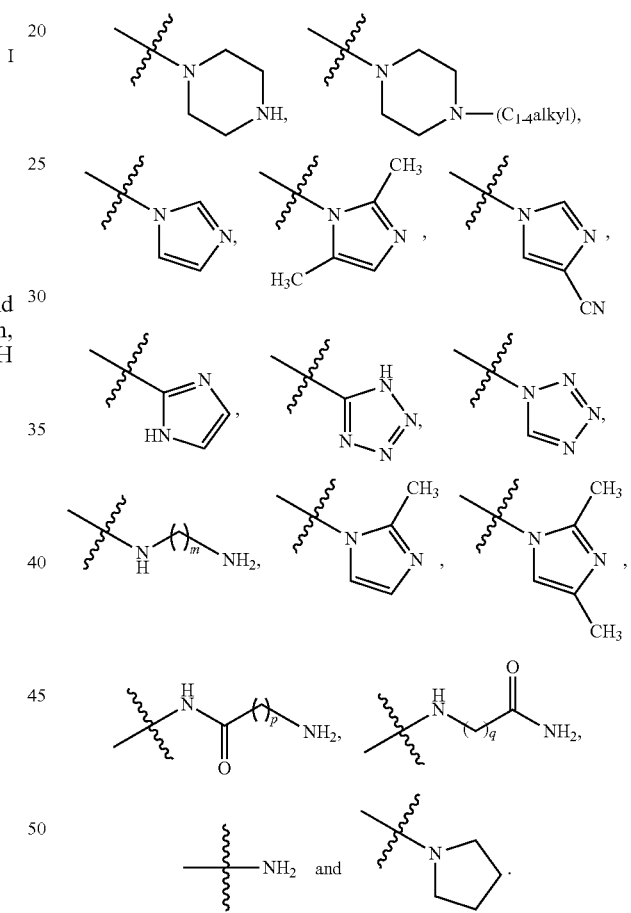

In yet another embodiment of the application, $R^3$ is piperazinyl.

In another embodiment, $R^3$ in the compounds of Formula I is

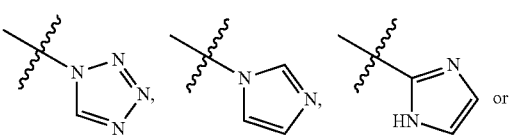

-continued

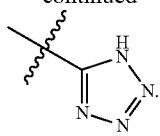

In another embodiment, R³ in the compounds of Formula I is

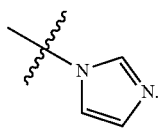 [SMILES: *n1ccnc1]

In another embodiment, R³ in the compounds of Formula I is

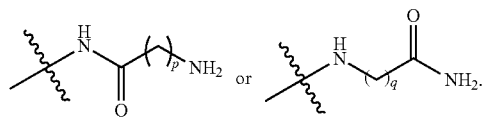

In another embodiment, n in the compounds of Formula I is 1 or 2.

In another embodiment, m in the compounds of Formula I is 1 or 2.

In another embodiment, p and q in the compounds of Formula I is 1.

In a further embodiment of the application, the compound of Formula I is a compound of Formula (Ib):

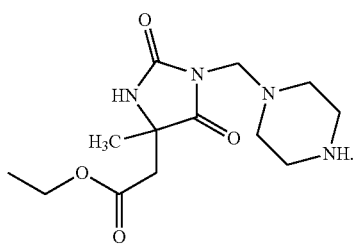

In yet a further embodiment of the application, the compound of Formula I is a compound of Formula (Ic):

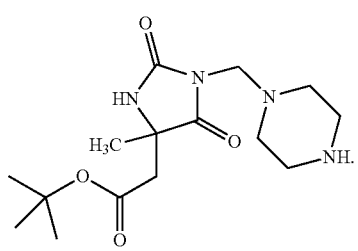

In yet a further embodiment of the application, the compound of Formula I is a compound of Formula (Ig):

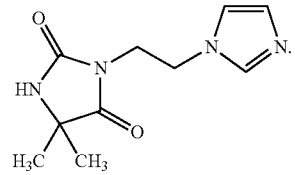

In yet a further embodiment of the application, the compound of Formula I is a compound of Formula (Ih):

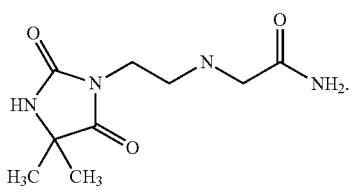

In a further embodiment, the compounds of Formula I are acid addition salts. In a further embodiment, the acid salt is a trifluoroacetic acid salt. In another embodiment, the acid salt is a hydrochloric acid salt.

The preparation of the compounds of the application can be performed using methods known in the art using solvents and reagents obtained from commercial sources. For example, a suitable compound of Formula II:

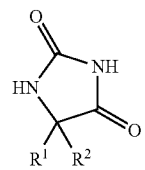

wherein $R^1$ and $R^2$ are independently selected from $C_{1-6}$alkyl and $C_{1-4}$alkyleneR⁴; wherein R⁴ is selected from COOR⁵, Ph, $C_{3-6}$cycloalkyl and NHR⁶; wherein R⁵ is selected from H and $C_{1-6}$alkyl, and R⁶ is selected from H, Ac and Bz; is reacted with suitable reagents under conditions suitable to form a compound of Formula I:

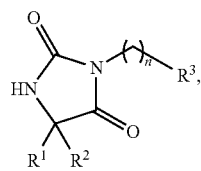

wherein $R^1$ and $R^2$ are independently selected from $C_{1-6}$alkyl and $C_{1-4}$alkyleneR⁴; wherein R⁴ is selected from COOR⁵, Ph, $C_{3-6}$cycloalkyl and NHR⁶; wherein R⁵ is selected from H and $C_{1-6}$alkyl, and R⁶ is selected from H, Ac and Bz;

$R^3$ is selected from:

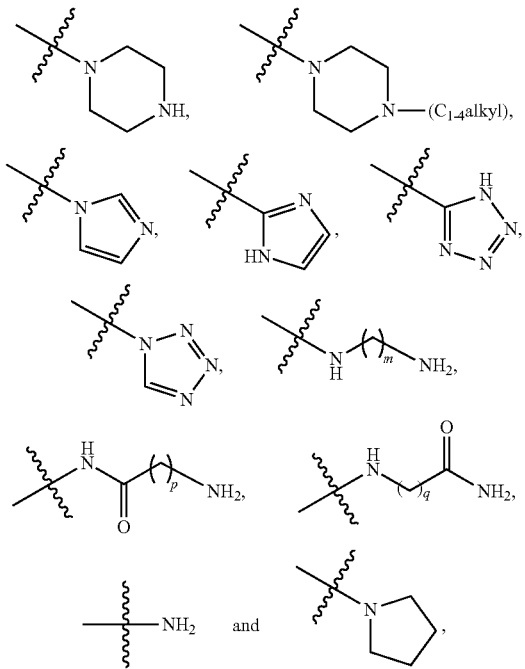

in which any one of the available hydrogen atoms on $R^3$ is optionally substituted with $C_{1-4}$alkyl or cyano; and m, n, p, and q are, independently, 1, 2 or 3, The identity of the suitable reagents for reaction with the compounds of Formula II to obtain the compounds of the application would be known to a person skilled in the art based on the desired values for n and $R^3$. For example, to prepare a compound of Formula (Ia):

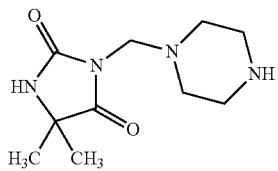

a suitable amount of piperazine is added to a solution of a suitable amount of 5,5-dimethylhydantoin in a suitable solvent, for example ethanol at, for example, about room temperature, and the reaction mixture allowed to heat at a suitable temperature, for example at about 20° C. to about 150° C. or about 70° C., then a suitable amount of formaldehyde is added dropwise, and the reaction mixture allowed to stir for a time for the conversion of the reactants to the compound of Formula (Ia) to proceed to a sufficient extent, for example about 0.1 hour to about 24 hours, or about 1 hour.

The compounds of Formula II may be commercially available, for example 5,5-dimethylhydantoin is available from Sigma-Aldrich™. The compounds of Formula II may also be prepared using methods known in the art. For example, the compound of the Formula (IIb):

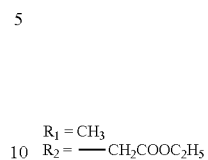

$R_1 = CH_3$
$R_2 = -CH_2COOC_2H_5$ is prepared by heating suitable amounts of ethylacetoacetate, ammonium carbonate and potassium cyanide in a suitable solvent, for example, 50:50 ethanol:water at a suitable temperature, for example at about 20° C. to about 150° C., or about 75° C. for a time for the conversion of the reactants to the compound of Formula (IIb) to proceed to a sufficient extent, for example about 1 hour to about 48 hours, or about 18 hours in a suitable reaction vessel, for example, a sealed pressure tube.

The preparation of salts of the compounds of the application can also be performed by methods known in the art. For example, a solution of a suitable acid, for example, trifluoroacetic acid in a suitable solvent, for example dichloromethane can be added dropwise to a suitable amount of a solution of a compound of Formula I in a suitable solvent, for example, dichloromethane at a suitable temperature, for example at about −20° C. to about 20° C., or about 0° C., the reaction mixture stirred for a time of about 0.1 hour to about 24 hours, or about one hour, the temperature increased to a temperature of about 0° C. to about 50° C., or about room temperature, and the reaction mixture stirred for a time for the conversion of the reactants to the salt of the compound of Formula I to proceed to a sufficient extent, for example about 0.1 hour to about 24 hours, or about one hour.

In some cases, the preparation methods outlined above may have to be modified, for instance by use of protective groups, to prevent side reactions due to reactive groups, such as reactive groups attached as substituents. This may be achieved by means of conventional protecting group methodologies.

The following non-limiting examples are illustrative of the present application:

EXAMPLES

General Materials and Methods

All anhydrous reactions were performed under a nitrogen atmosphere. All solvents and reagents were obtained from commercial sources; anhydrous solvents were prepared following standard procedures. Reaction progress was monitored by TLC (Silica gel-60 $F_{254}$) plates. Chromatographic purifications were performed using silica gel (60 Å, 70-230 mesh) and final products were purified by LC/MS on a Waters LC/MS system equipped with a photodiode array detector using an XBridge semi-preparative C18 column (19.2 mm×150 mm, 5 µm I.D.). Mass spectra were recorded using ESI (+ve) mode. All HPLC solvents were filtered through Waters membrane filters (47 mm GHP 0.45 µm, Pall Corporation). Injection samples were filtered using Waters Acrodisc® Syringe Filters 4 mm PTFE (0.2 µm). NMR spectra were recorded on a Bruker spectrometer (400 MHz for $^1H$). Chemical shifts were reported in δ ppm using tetramethylsilane (TMS) as a reference for the $^1H$ NMR spectra.

Example 1: Preparation of the Compound of Formula (Ia): 5,6-Dimethyl-3-(piperazin-1-ylmethyl)imidazolidin-2,4-dione

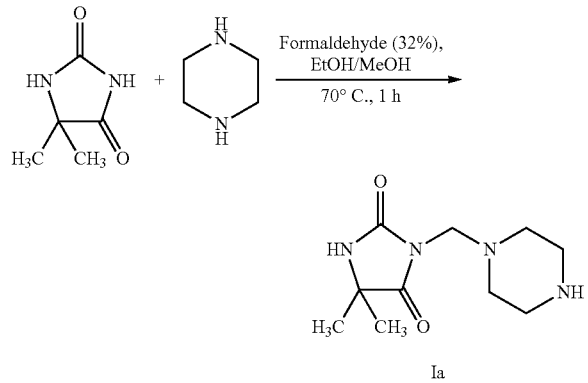

Piperazine (1.41 g, 16.3 mmol) was added to a solution of 5,5-dimethylhydantoin (2.0 g, 15.6 mmol) in 30 mL of alcohol at room temperature, and the reaction mixture was allowed to heat at 70° C. Formaldehyde (36% in H₂O, 1.68 mL) was added dropwise to the reaction mixture at 70° C. and the heating was continued for 1 h. The completion of the reaction was monitored by Alumina TLC using 10% MeOH in DCM as mobile phase. The reaction mixture was cooled to room temperature and the solvents were evaporated to dryness. The residue was taken up in ethyl acetate (40 mL) and the mixture was washed with water (20 mL). The organic phase was separated, dried over anhydrous sodium sulfate and the solvents were evaporated under vacuum to afford pure compound of Formula (Ia) (2.4 g, 68%).

$^1$H NMR (CDCl$_3$, 400 MHz): δ 1.44 (s, 6H), 2.49-2.61 (m, 8H), 4.44 (s, 2H); ESI m/z [M+1H]$^+$ Found: 227.14. Purity>95%.

Example 2: Preparation of the TFA Salt of the Compound of Formula (Ia)

To the compound of Formula (Ia) (100 mg, 0.44 mmol) in anhydrous dichloromethane (20 mL), a solution of trifluoroacetic acid (1.0 eq) in dichloromethane (5 mL) was added dropwise at 0° C. and the mixture was stirred at the same temperature for one hour. The reaction mixture was brought to room temperature and stirred for one more hour. The solvent was evaporated to dryness and the residue was triturated with diethyl ether to afford the pure TFA-salt of the compound of Formula (Ia).

$^1$H NMR (D$_2$O, 400 MHz): δ 1.47 (s, 6H), 2.99 (t, 4H), 3.33 (t, 4H), 4.26 (s, 2H); ESI m/z 227.20 [M+1H]$^+$.

Example 3: Preparation of the Compound of Formula (IIb): Ethyl (4-methyl-2,5-dioxoimidazolidin-4-yl)acetate

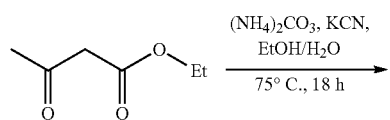

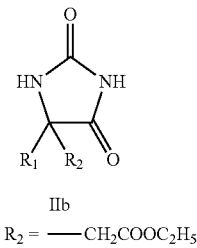

IIb
R$_1$ = CH$_3$, R$_2$ = ——CH$_2$COOC$_2$H$_5$

Ethylacetoacetate (1.96 mL, 15.3 mmol), ammonium carbonate (4.42 g, 46 mmol)) and potassium cyanide (1.5 g, 23 mmol) in ethanol/water (20 mL, 50:50) was heated at 75° C. for 18 h in a sealed pressure tube. The reaction mixture was cooled at room temperature and the volatiles were removed under vacuum. The residue was taken in ethyl acetate (20 mL), washed with water (20 mL), dried over anhydrous sodium sulfate and evaporated to dryness to afford the compound of Formula (IIb) as a white solid (745 mg, 21%).

$^1$H NMR (DMSO-D$_6$, 400 MHz): δ 1.15 (t, J=7.10 Hz, 3H), 1.25 (s, 3H), 2.54 (d, J=16.29 Hz, 1H), 2.81 (d, J=16.21 Hz, 1H), 4.02 (m, 2H), 7.88 (s, 1H), 10.61 (s, 1H).

Example 4: Preparation of the Compound of Formula (Ib): Ethyl [4-methyl-2,5-dioxo-1-(piperazin-1-ylmethyl)imidazolidin-4-yl]acetate

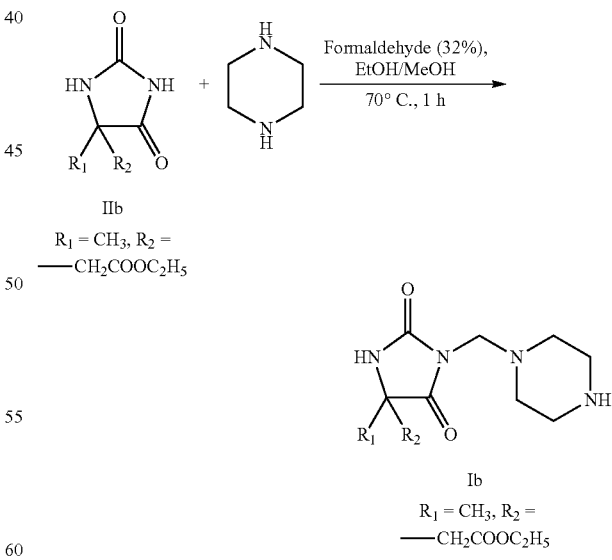

The compound of Formula (Ib) was synthesized using the same method described for the compound of Formula (Ia).

$^1$H NMR (CDCl$_3$, 400 MHz): δ 1.26 (t, J=6.90 Hz, 3H), 1.51 (s, 3H), 2.44-2.85 (m, 8H), 4.17 (q, 2H), 4.45 (s, 2H), 5.91 (s, 1H).

Example 5: Preparation of the Compound of Formula (IIc): tert-Butyl (4-methyl-2,5-dioxoimidazolidin-4-yl)acetate

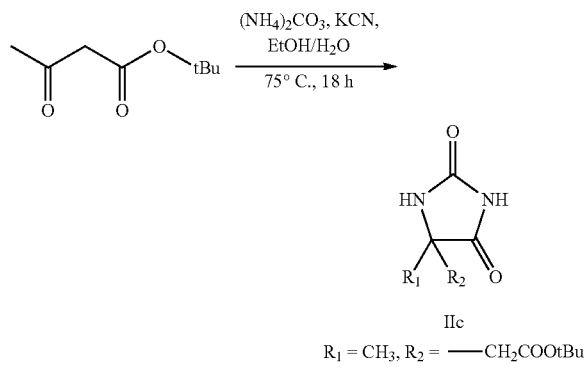

The compound of Formula (IIc) (740 mg, 32%) was synthesized following the same procedure described for the compound of Formula (IIb), starting with t-butylacetoacetate (1.66 mL, 10 mmol).

$^1$H NMR (DMSO-$d_6$, 400 MHz): δ 1.22 (s, 3H), 1.35 (s, 9H), 2.39 (d, J=15.89 Hz, 1H), 2.76 (d, J=15.53 Hz, 1H), 7.91 (s, 1H), 10.59 (s, 1H).

Example 6: Preparation of the Compound of Formula (Ic): tert-Butyl-[4-methyl-2,5-dioxo-1-(piperazin-1-ylmethyl)imidazolidin-4-yl]acetate

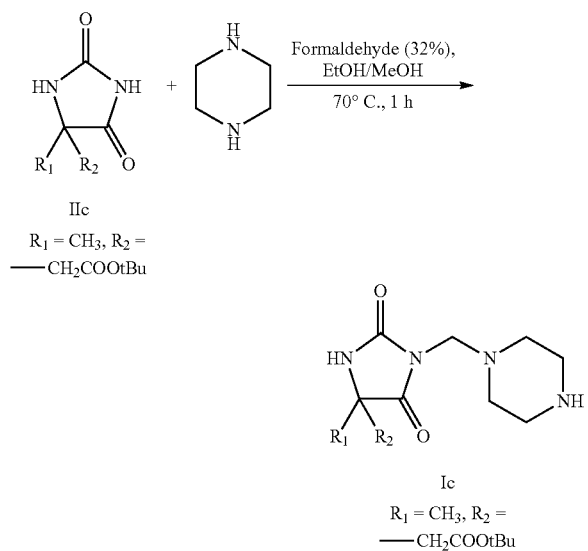

The compound of Formula (Ic) was synthesized using the same method described for the compound of Formula (Ia).

$^1$H NMR (CDCl$_3$, 400 MHz): δ 1.43 (s, 9H), 1.67 (s, 3H), 2.45 (s, 2H), 2.62-2.70 (m, 8H), 4.45 (d, J=13.73 Hz, 2H), 6.09 (s, 1H).

Example 7: Inhibition of PAD4 Activity by the Compound of Formula (Ia)

The compound of Formula I(a) was evaluated for its inhibition of PAD4 enzyme activity in vitro at 30 μM concentration. Inhibition of PAD4 was estimated at 37° C. in the presence of 30 μM of the compound. The inhibitor as mixed with the substrate N-α-benzoyl L-arginine ethyl ester (BAEE) solution and preincubated at 37° C. for 10 minutes. The control reaction contained no inhibitor. The enzyme was added to initiate the reaction. The reaction samples were incubated at 37° C. for 30 minutes. Color reagent was added and the samples were boiled for 15 minutes. Samples were cooled on ice, further processed, and the absorbance was measured at 530 nm. Remaining activity was calculated as a percentage of the uninhibited samples. The compound of Formula (Ia) showed encouraging results, with 78% Inhibition of the enzyme activity.

The compound of Formula (Ia) was further investigated by synthesizing a small number of derivatives and conducting additional enzymology experiments. In parallel, an in vivo study was carried out using the compound of Formula (Ia) in an MOG-EAE mouse model to investigate efficacy. Below, these results are described briefly.

Example 8: Additional Enzymology Experiments on the Compounds of Formula I(a), Formula I(b) and Formula I(c)

The IC$_{50}$ for the compound of Formula (Ia) against rabbit PAD2 was 24.1±2.8 μM and that of human PAD4 was 48.3±7.4 μM (Table 1). Further enzymology revealed that the equilibrium inhibition constant $K_i$ against PAD2 is 930 nM and that of human PAD4 is 7.4 μM, a potent molecule against these enzymes in vitro. Evaluation of the PAD inhibitory activities of compounds of Formula (Ib) and (Ic) was carried out (Table 1). The compound of Formula (Ib) inhibited PAD2 with $K_i$ of 460 nM. The compound of Formula (Ic) inhibited PAD2 with a $K_i$ of 650 nM. When evaluated against human PAD4, the compound of Formula (Ib) exhibited a $K_i$ of 11.7 μM.

Example 9: Mouse Toxicity Studies

There was no general toxicity observed in mice when dosed with 10 mg/mouse of the compound of Formula (Ia) for 5 days, or a single 20 mg/mouse dose of the compound of Formula (Ia) providing assurance that the compound of Formula (Ia) can be considered for in vivo efficacy studies.

Example 10: MOG-EAE Mouse Model

Figure 8:
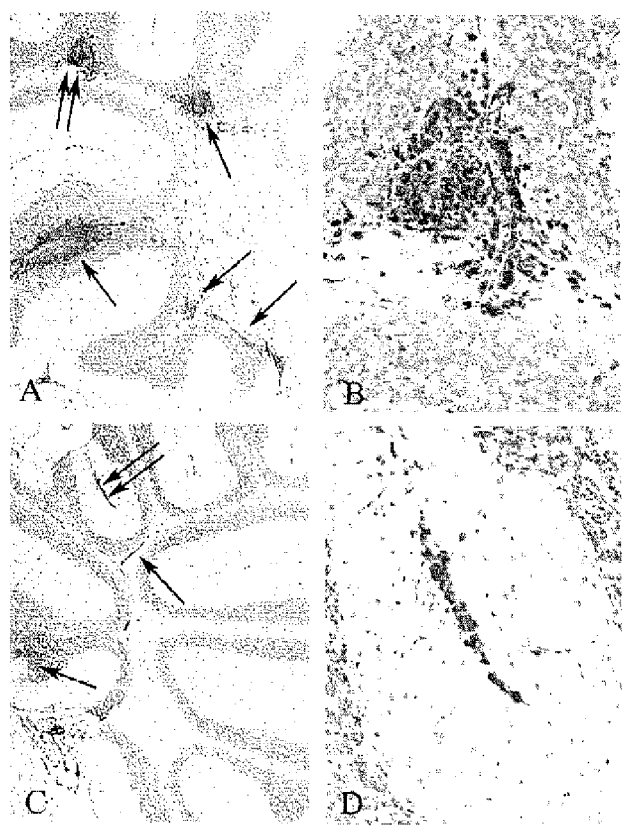
FIG. 8 shows (A) Cerebellum from an untreated MOG-EAE mouse. Arrows indicate CD3 +ve cells (40× magnification). (B) Vessel (highlighted by double arrows in panel A) surrounded by CD3 +ve cells at 400× magnification. (C) Cerebellum from MOG-EAE mouse treated with the compound of Formula (Ia). Note the areas with fewer CD3 +ve cells in comparison to the untreated animal and contrast with panel A (40× magnification). (D) Vessel (double arrows in panel C) surrounded by CD3 +ve cells at 400× magnification.

A MOG-EAE mouse model (C57BL/6 mice, n=5) was used to investigate the efficacy of the compound of Formula (Ia). On day 8 after the induction of EAE, mice received 2 mg of the compound of Formula (Ia) b.i.d. (i.p.) every other day until day 23. There was a clear improvement in the clinical scores in the mice receiving the compound of Formula (Ia) (clinical scores improving to almost 1 with a limping tail, in comparison to the control group score at higher than 2 with inability to righting). Mice were sacrificed on day 24 (i.e. after 2 weeks of treatment) and anti-CD3 staining on spinal cord and brain samples was undertaken. In brain, untreated mice showed CD3 markers at 4.8±0.19/mm$^2$ vs. in the compound of Formula (Ia)-treated samples, it was 3.8±0.23/mm$^2$ (significance level>0.015), with a clear reduction in the CD3 +ve T cells in the treated brain samples with most marked reduction in cerebellum (FIG. 8), and much reduced PAD activity. These preliminary observations indicated that immune response has decreased after treatment with PAD inhibitors as a result of the inhibition of citrullination.

The above results suggest that inhibitors such as the compound of Formula (Ia), which are non-substrate analogs, provide structural features of significance for the development of inhibitors targeting deiminases and exhibit in vivo efficacy in animal models improving the symptoms associated with the demyelinating diseases such as MS. In order to target PAD enzyme activity and demyelination, it was hypothesized that PAD2 and PAD4 isozymes will be important because these two isozymes are predominately expressed in CNS and are seen at elevated levels in brain in MS. PAD2 and PAD4 isozymes share 50% identity among their sequences.

Figure 9:
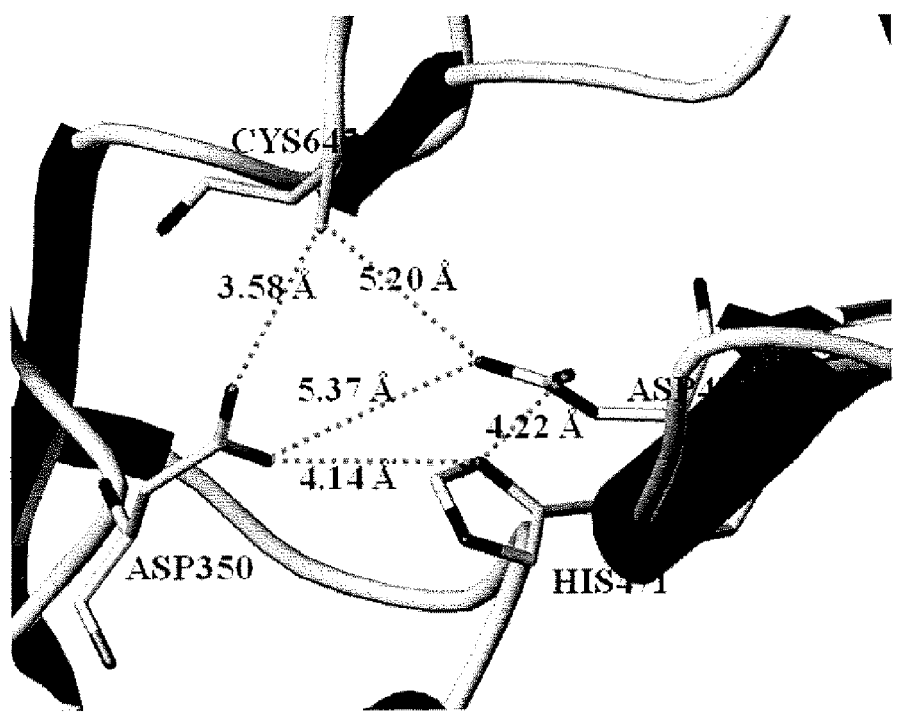
FIG. 9 shows (A) Architecture of the catalytic residues in the active site of PAD4, and the distance between important functional side chains of the catalytic residues. (B) Structure of the compound of Formula (Ia) (left panel). The compound of Formula (Ia) bound in the binding site of PAD4, as predicted in in silico docking (right panel). Crystal structure of PAD4 is used as a template for the in silico screening (PDB code: 1WDA). A portion of the binding site is shown as a Connolly surface, the inhibitor in a ball-and-stick model and the residues are shown as capped-stick model. (C) PAD4 binding pocket with extended tunnel. Residues around the tunnel are shown as capped-stick model.
Figure 9:
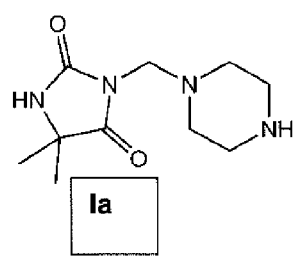
Figure 9:
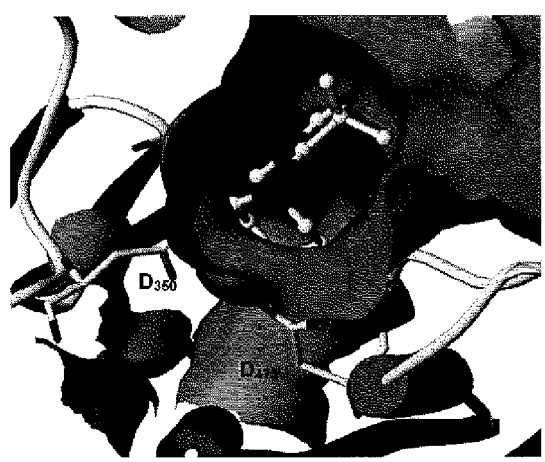
Figure 9:
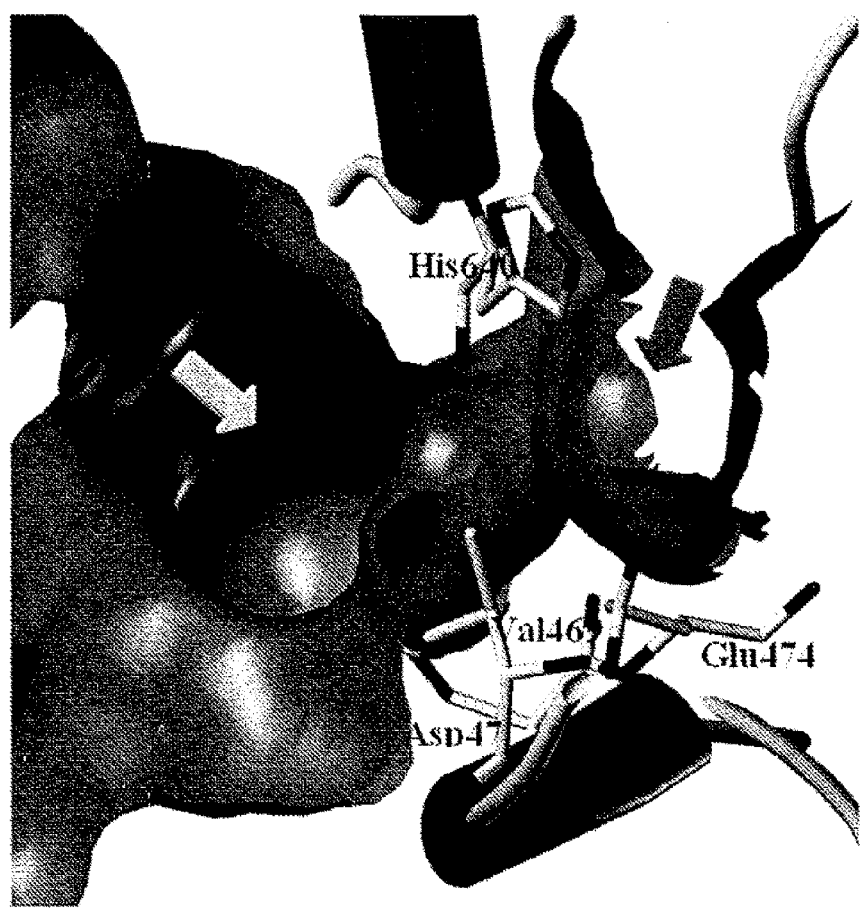

The quest of the present application for novel ligands and structure-based investigations initially led to the study on the three-dimensional structure of PAD enzymes. When one looks at the architecture of the catalytic site and the binding of the substrate (peptidyl Arg), it is conceivable that the guanidinium moiety of Arg residue interacts with the two Asp residues (Asp350, Asp 473), catalytic Cys645 and His471 residues, altogether forming the catalytic tetrad to carry out the hydrolysis of the guanidinlum moiety to yield citrulline (FIG. 9A).[59]

Example 11: Preparation of Further Compounds of Formula I

The following additional compounds of Formula I have been prepared using procedures analogous to those described in Examples 1-6:

| Compound No. | n | R³ |
|---|---|---|
| I(d) | 2 | —N(piperazine)NH |
| I(e) | 1 | —N(piperazine)NCH₃ |
| I(f) | 2 | —N(pyrrolidine) |
| I(g) | 2 | —N(imidazole) |
| I(h) | 2 | —NH—CH₂—C(=O)NH₂ |
| I(i) | 2 | —NH₂ |
| I(j) | 2 | —NH—CH₂CH₂—NH₂ |
| I(k) | 3 | —NH₂ |
| I(l) | 3 | —NH—CH₂CH₂—NH₂ |

Based on the structural analysis and the PAD inhibition activities observed thus far, the following structures of Formula I are considered to be potential inhibitors of PAD activities, thus with potential in the treatment of diseases caused due to hypercitrullination due to hyperactivity of PAD enzymes such as multiple sclerosis, rheumatoid arthritis, Alzheimer's etc.:

Formula I $n = 1-3$

| R₁ | R₂ |
|---|---|
| —CH₃ | —CH₃ |
| —CH₂CH₃ | —CH₂CH₃ |
| —CH₂Ph | —CH₂Ph |
| —i-Pr | —i-Pr |
| —t-Bu | —t-Bu |
| —i-pentyl | —i-pentyl |
| —CH₂COOC₂H₅ | —CH₂COOC₂H₅ |
| —CH₂COOtBu | —CH₂COOtBu |
| —CH₂CH₂CO₂H | —CH₂CH₂CO₂H |
| —C₃H₆COOH | —C₃H₆COOH |
| —CH₂—Ph | —CH₂—Ph |
| —CH₂CH₂—Ph | —CH₂CH₂—Ph |
| —CH₂-cycloHexyl | —CH₂-cycloHexyl |
| —CH₂CH₂NH₂ | —CH₂CH₂NH₂ |
| —CH₂CH₂CH₂NH₂ | —CH₂CH₂CH₂NH₂ |
| —CH₂CH₂NHAc | —CH₂CH₂NHAc |
| —CH₂CH₂NHBz | —CH₂CH₂NHBz |
| —CH₂CH₂CH₂NHAc | —CH₂CH₂CH₂NHAc |
| —CH₂CH₂CH₂NHBz | —CH₂CH₂CH₂NHBz |

-continued

R₃

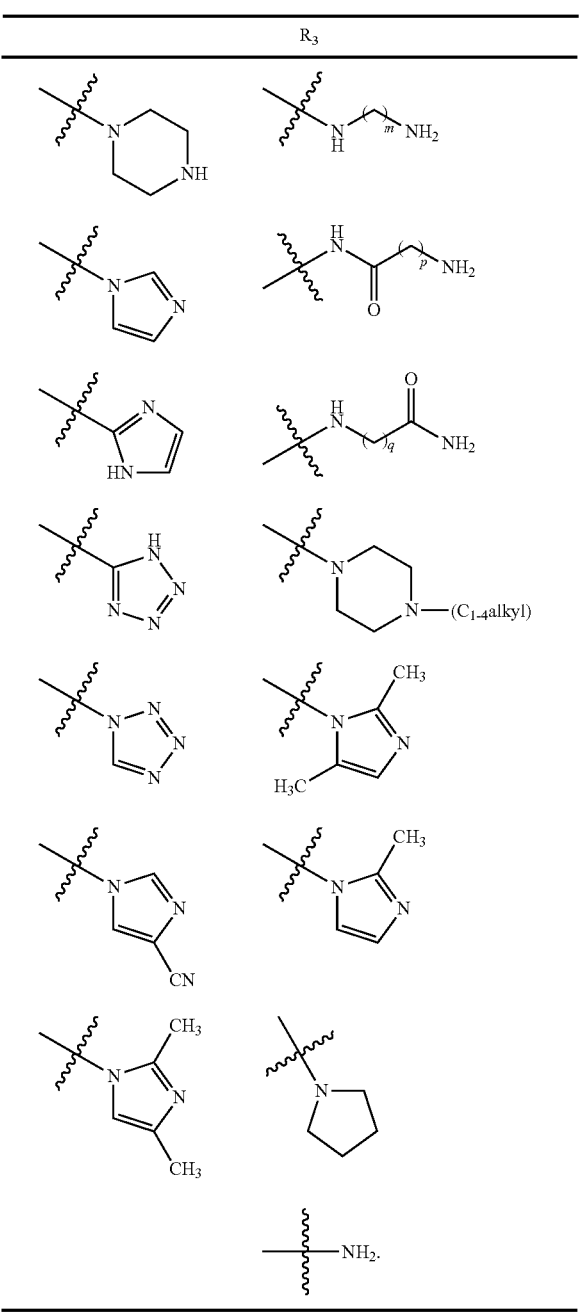

m, p and q = (independently) 1, 2 or 3

Example 12: Inhibition of PAD1, PAD2 and PAD4 by Further Compounds of the Application The inhibition of human PAD1, PAD2 and PAD4 was estimated at 37° C. in the presence of 50 and 1000 μM of each inhibitor tested. The inhibitor was mixed with the substrate N-α-benzoyl L-arginine ethyl ester (BAEE) solution and preincubated at 37° C. for 10 min. Control reaction contained no inhibitor. Enzyme was added to initiate the reaction. The reaction samples were incubated at 37° C. for 30 min. Color reagent was added and the samples were boiled for 15 min. Samples were cooled on ice, further processed, and the absorbance was measured at 530 nm. Remaining activity was calculated as a percentage of the uninhibited samples.

Figure 10:
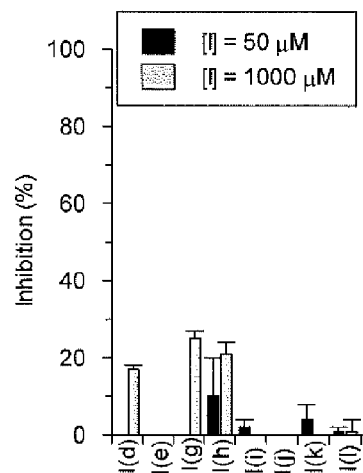
FIG. 10 shows the inhibition of (A) PAD1 and (B) PAD4 by compounds of Formula I(d)-I(l) in exemplary embodiments of the present application. Two separate inhibitor concentrations were used at a fixed concentration of enzyme.
Figure 10:
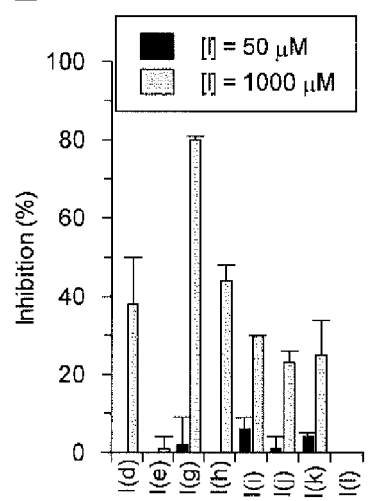
Figure 11:
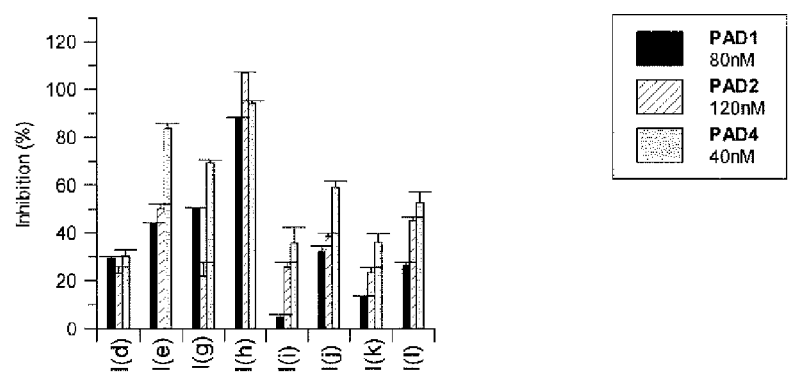
FIG. 11 shows the inhibition of PAD1, PAD2 and PAD4 by TFA salts of compounds of Formula I(d)-I(l) in exemplary embodiments of the present application. Inhibitor concentration was (A) 1 mM and (B) 50 µM.
Figure 11:
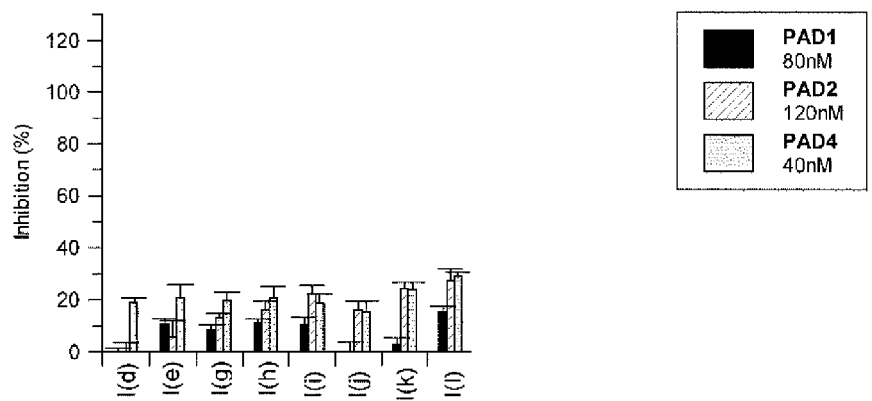

FIG. 10 shows the inhibition of PAD1 and PAD4 at various concentrations of compounds I(d)-I(l). FIG. 11 shows the inhibition of PAD1, PAD2 and PAD4 at various concentrations of compounds I(d)-I(l). Table 2 shows the inhibition constants ($K_i$) for these compounds against PAD1, PAD2 and PAD4, as well as the in vitro cellular toxicity to CHO cells.

Among these compounds, I(h) showed good activity against PAD4, in comparison to PAD1. Compound I(g) inhibited PAD4 with a higher potency (i.e. $K_i$ was lower, 4.0±1.7 μM) than it did PAD1. These compounds were tested either as free bases or the corresponding TFA salts. In general, TFA salts where relevant and appropriate, improved their aqueous solubility and were more potent inhibiting the PAD activity.

The other compounds I(d), I(e), I(i), I(j), I(k), I(l) were either moderate or weak inhibitors of PAD1 and PAD4 enzymes (Table 2). A N-methyl group on the piperazine moiety as in I(e) reduced the inhibition of PAD enzymes (compare I(a) vs (Ie)). Similarly a simple amino alkyl moiety on the hydantoin (such as in I(i) and I(k)) did not yield higher potency compounds, but hydanoins with two amino moieties (one terminal primary amino moiety and one in the form of a secondary amine) as in I(j) and I(l) were moderately potent to inhibit PAD enzymes.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| Deiminase | Compound | $IC_{50}$ (μM) | $K_i$ (μM) |
|---|---|---|---|
| PAD2 | Formula (Ia) | 482 | 0.93 |
| PAD4 | Formula (Ib) | 12.3 ± 4.8 | 0.46 |
| | Formula (Ic) | 16.8 ± 7.0 | 0.65 |
| | Formula (Ia) | 48.3 ± 7.4 to 3,821.5 ± 181.6* | 4.2 ± 0.5 to 331.7 ± 16.8* |
| | Formula (Ib) | 36.0 ± 18.0 | 3.1 ± 1.6 |
| | Formula (Ic) | NA | NA |
| PAD1 | Formula (Ia) | 763 | |

*Inhibition varies depending on the salt form (such as trifluoroacetate, hydrochloride or free base) and the batch of the enzyme.

TABLE 2

| | PAD $K_i$ ± SE (μM) | | CHO cells |
|---|---|---|---|
| Compound | PAD1 | PAD4 | $IC_{50}$ ± SE (μM) |
| I(e) | 114.5 ± 5.5 | 45.6 ± 9.0 | 143 ± 4 |
| I(g) | 109.7 ± 4.0 | 4.0 ± 1.7 | 1991 ± 823 |
| I(h) | 33.6 ± 2.6 | 21.8 ± 7.1 | ND |
| I(i) | 117.4 ± 41.1 | 317 ± 32.8 | 5841 ± 2369 |
| I(j) | 55.5 ± 12.3 | 52 ± 34.1 | 2693 ± 175 |
| I(k) | 104.6 ± 22.1 | 384 ± 41.0 | ND |
| I(l) | 42.9 ± 5.0 | 123 ± 14.7 | 16725 ± 31609 |

FULL CITATIONS FOR DOCUMENTS REFERRED TO IN THE SPECIFICATION

1. Popescu, B. F.; Lucchinetti, C. F. Pathology of demyelinating diseases. *Annu. Rev. Pathol.* 2012, 7, 185-217.
2. Dutta, R.; Trapp, B. D. Pathogenesis of axonal and neuronal damage in multiple sclerosis. *Neurology* 2007, 68(2), S22-S31.
3. Noseworthy, J. H. Progress in determining the causes and treatment of multiple sclerosis. *Nature* 1999, 399, A40-A47.
4. Aluord, E. C. Acute disseminated encephalomyelitis and allergic encephalopathies. In Vinken P. I., Bruyan G. W. Handbook of clinical neurology, New York, N.Y., Elsevier. 1970, 9, 560-571.
5. Hashim, G. A.; Wood, D. D.; Moscarello, M. A. Myelin lipophilin induced demyelinating diseases of the central nervous system. *Neurochem. Res.* 1980, 5, 1117-1115.
6. Sospedra, M.; Martin, R. Immunology of multiple sclerosis. *Annu. Rev. Immunol.* 2005, 23, 683-747.
7. Lebar, R.; Lubetzki, C.; Vincent, C.; Lombrail, P.; Boutry, J. M. The M2 autoantigen of central nervous system myelin, a glycoprotein present in oligodendrocyte membrane. *Clin. Exp. Immunol.* 1986, 66(2), 423-434.
8. Bahreini, S. A.; Jabalameli, M. R.; Saadatnia, M.; Zahednasab, H. The role of non-HLA single nucleotide polymorphisms in multiple sclerosis susceptibility. *J. Neuroimmunol.* 2010, 229, 5-15.
9. Steinman, L.; Zamvil, S. S. Multiple sclerosis in need of a critical reappraisal. *Med. Hypothesis.* 2006, 54, 99-106.
10. Lopez-Diego, R. S.; Weiner, H. L. Novel therapeutic strategies for multiple sclerosis—a multifaceted adversary. *Nature Rev. Drug Discov.* 2008, 7, 909-925.
11. Weinstock-Guttman, B.; Jacobs, L D. What is new in the treatment of multiple sclerosis. *Drugs* 2000, 59, 401-410.
12. Amon, R.; Aharoni, R. Mechanism of action of glatiramer acetate in multiple sclerosis and its potential for the development of new applications. *Proc. Natl. Acad. Sci. USA* 2004, 101 Suppl. 2, 14593-14598.
13. Toker, A.; Slaney, C. Y.; Bäckström, B. T.; Harper, J. L. Glatiramer acetate treatment directly targets CD11 b(+) Ly6G(-) monocytes and enhances the suppression of autoreactive T cells in experimental autoimmune encephalomyelitis. *Scand. J. Immunol.* 2011, 74, 235-243.
14. Yeh, E. A. Current therapeutic options in pediatric multiple sclerosis. *Curr. Treat. Options Neurol.* 2011, 13, 544-559.
15. Merck KGaA pulls plug on cladribine on FDA feedback. *Reuters News.* Jun. 22, 2011, http://www.reuters.com/article/2011/06/22/merckkgaa-cladribine-idUSLDE75L05020110622.
16. Quirke, A. M.; Fisher, B. A.; Kinloch, A. J.; Venables, P. J. Citrullination of autoantigens: upstream of TNFα in the pathogenesis of rheumatoid arthritis. *FEBS Lett.* 2011, 585(23), 3681-3688.
17. Lange, S.; Gögel, S.; Leung, K. Y.; Vemay, B.; Nicholas, A. P.; Causey, C. P.; Thompson, P. R.; Greene, N. D.; Ferretti, P. Protein deiminases: new players in the developmentally regulated loss of neural regenerative ability. *Dev. Biol.* 2011, 355(2), 205-214.
18. Kidd, B. A.; Ho, P. P.; Sharpe, O.; Zhao, X.; Tomooka, B. H.; Kanter, J. L.; Steinman, L.; Robinson, W. H. Epitope spreading to citrullinated antigens in mouse models of autoimmune arthritis and demyelination. *Arthritis Res. Ther.* 2008, 10, R119.
19. Harauz, G.; Musse, A. A. A tale of two citrullines-structural and functional aspects of myelin basic protein deimination in health and disease. *Neurochem. Res.* 2007, 32, 137-158.
20. Vossenaar, E. R.; Zendman, A. J.; van Venrooij, W. J.; Pruijn, G. J. PAD, a growing family of citrullinating enzymes: genes, features and involvement in disease. *Bioessays* 2003, 25(11), 1106-1118.
21. Mastronardi, F. G.; Wood, D. D.; Mei, J.; Raljmakers, R.; Tseveleki, V.; Dosch, H. M.; Probert, L.; Casaccia-Bonnefll, P.; Moscarello, M. A. Increased citrullination of histone H3 in multiple sclerosis brain and animal models of demyelination: a role for tumor necrosis factor-induced peptidylarginine deiminase 4 translocation. *J. Neurosci.* 2006, 26, 11387-11396.
22. Moscarello, M. A.; Wood, D. D.; Ackerley, C.; Boulias, C. Myelin in multiple sclerosis is developmentally immature. *J. Clin. Invest* 1994, 94, 146-154.
23. Wood, D. D.; Bilbao, J. M.; O'Connors, P.; Moscarello, M. A. Acute multiple sclerosis (Marburg type) is associated with developmentally immature myelin basic protein. *Ann. Neurol.* 1996, 40, 18-24.
24. Brady, G. W.; Fein, D. B.; Wood, D. D.; Moscarello, M. A. The interaction of basic proteins from normal and multiple sclerosis myelin with phosphatidylglycerol vesicles. *FEBS Lett.* 1981, 125, 159-160.
25. Brady, G. W.; Murthy, N. S.; Fein, D. B.; Wood, D. D.; Moscarello, M. A. The effect of basic myelin protein on multilayer membrane formation. *Biophys. J.* 1981, 34(2), 345-350.
26. Boggs, J. M.; Wood, D. D.; Moscarello, M. A. Hydrophobic and electrostatic interactions of myelin basic proteins with lipid. Participation of N-terminal and C-terminal portions. *Biochemistry* 1981, 20(5), 1065-1073.
27. Epand, R. M.; Moscarello, M. A.; Zierenberg, B.; Vail, W. J. The folded conformation of the encephalitogenic protein of the human brain. *Biochemistry* 1974, 13, 1264-1267.
28. Deber, C. M.; Hughes, D. W.; Fraser, P. E.; Pawagi, A. B.; Moscarello, M. A. Binding of human normal and multiple sclerosis-derived myelin basic protein to phospholipid vesicles: effects on membrane head group and bilayer regions. *Arch. Biochem. Biophys.* 1986, 245(2), 455-463.
29. Carrillo-Vico, A.; Leech, M. D.; Anderton, S. M. Contribution of myelin autoantigen citrullination to T cell autoaggression in the central nervous system. *J. Immunol.* 2010, 184 (6), 2839-2846.
30. Raijmakers, R.; Vogelzangs, J.; Croxford, J. L.; Wesseling, P.; van Venrooij, W. J.; Pruijn, G. J. Citrullination of central nervous system proteins during the development of experimental autoimmune encephalomyelitis. *J. Comp. Neurol.* 2005, 486(3), 243-253.
31. Gyorgy, B.; Toth, E.; Tarcsa, E.; Falus, A; Buzas, E. I. Citrullination: a posttranslational modification in health and disease. *Int. J. Biochem. Cell. Biol.* 2006, 38 (10), 1662-1677.
32. Curls, E.; Nicolis, I.; Moinard, C.; Osowska, S.; Zerrouk, N.; Benazeth, S.; Cynober, L. Almost all about citrulline in mammals. *Amino Acids* 2005, 29 (3), 177-205.
33. Vossenaar, E. R.; Zendman, A. J.; van Venrooij, W. J.; Pruijn, G. J. PAD, a growing family of citrullinating enzymes: genes, features and involvement in disease. *Bioessays* 2003, 25(11), 1106-1118.
34. Anzilotti, C.; Pratesi, F.; Tommasi, C.; Migliorini, P. Peptidylarginine deiminase 4 and citrullination in health and disease. *Autoimmun Rev.* 2010, 9(3), 158-160.

35. Anzilotti, C.; Pratesi, F.; Tommasi, C.; Migliorini, P. Peptidylarginine deiminase 4 and citrullination in health and disease. *Autoimmun Rev.* 2010, 9(3), 158-160.
36. Chirivi, R. G. S.; van Rosmale, J. W. G.; Jenniskens, G. J.; Pruijn, G. J.; Raats, J. M.-H. itrullination: A target for disease intervention in multiple sclerosis and other inflammatory disorders. *J. Clin. Cell. Immunol.* 2-13, 4, 3.
37. Carrillo-Vico, A.; Leech, M. D.; Anderton, S. M. Contribution of myelin autoantigen citrullination to T cell autoaggression in the central nervous system. *J. Immunol.* 2010, 184(6), 2839-2846.
38. Musse, A. A; Harauz, G. Molecular "negativity" may underlie multiple sclerosis: role of the myelin basic protein family in the pathogenesis of MS. *Int Rev. Neurobiol.* 2007, 79, 149-172.
39. Deraos, G.; Chatzantoni, K.; Matsoukas, M. T.; Tselios, T.; Deraos, S.; Katsara, M.; Papathanasopoulos, P.; Vynios, D.; Apostolopoulos, V.; Mouzaki, A.; Matsoukas, J. Citrullination of linear and cyclic altered peptide ligands from myelin basic protein (MBP(87-99)) epitope elicits a Th1 polarized response by T cells isolated from multiple sclerosis patients: implications in triggering disease. *J. Med. Chem.* 2008, 51(24), 7834-7842.
40. Oguz, K. K.; Kume, A.; Aksu, A. O.; Karabulut, E.; Serdaroglu, A.; Teber, S.; Haspolat, S.; Senbil, N.; Kurul, S.; Anlar, B. Assessment of citrullinated myelin by 1H-MR spectroscopy in early-onset multiple sclerosis. *AJNR Am. J. {MNeuroradiol.* 2009, 30(4), 716-721.
41. Kidd, B. A.; Ho, P. P.; Sharpe, O.; Zhao, X.; Tomooka, B. H.; Kanter, J. L.; Steinman, L.; Robinson, W. H. Epitope spreading to citrullinated antigens in mouse models of autoimmune arthritis and demyelination. *Arthritis. Res. Ther.* 2008, 10(5), R119.
42. Raijmakers, R.; Vogelzangs, J.; Raats, J.; Panzenbeck, M.; Corby, M.; Jiang, H.; Thibodeau, M.; Haynes, N.; Van Venrooij, W. J.; Pruijn, G. J. M.; Werneburg, B. Experimental autoimmune encephalomyelitis induction in peptidylarginine deiminase 2 knockout mice. *J. Comp. Neurol.* 2006, 498, 217-226.
43. Guo, Q.; Bedford, M. T.; Fast, W. Discovery of peptidylarginine deiminase-4 substrates by protein array: antagonistic citrullination and methylation of human ribosomal protein S2. *Mol. Biosyst.* 2011, in press. PMID: 21584310
44. Wood, D. D.; Ackerley, C. A.; Brand, B.; Zhang, L.; Raijmakers, R.; Mastronardi, F. G.; Moscarello, M. A. Myelin localization of peptidylartginine deiminases 2 and 4: comparison of PAD2 and 4 activities. *Lab. Invest.* 2008, 88(4), 354-364.
45. Moscarello, M. A.; Mastronardi, F. G.; Wood, D. D. The role of citrullinated proteins suggests a novel mechanism in the pathogenesis of multiple sclerosis. *Neurochem. Res.* 2007, 32, 251-256.
46. Moscarello, M. A.; Lei, H.; Mastronardi, F. G.; Winer, S.; Tsui, H.; Li, Z.; Ackerley, C.; Zhang, L.; Raijmakers, R.; Wood, D. D. Inhibition of peptidylarginine deiminases reverses protein-hypercitrullination and disease in mouse models of multiple sclerosis. *Dis. Model. Mech.* 2013, 6(2), 467-478.
47. Nicholas, A. P.; Sambandam, T.; Echols, J. D.; Barnum, S. R. Expression of citrullinated proteins in murine experimental autoimmune encephalomyelitis. *J. Comp. Neurol.* 2005, 486, 254-266.
48. Lamensa, J. W.; Moscarello, M. A. Deimination of human myelin basic protein by a peptidylarginine deiminase from bovine brain. *J. Neurochem.* 1993, 61, 987-996.
49. Mastronardi, F. G.; Ackerley, C. A.; Arsenault, L.; Roots, B. I.; Moscarello, M. A. Demyelination in a transgenic mouse: a model for multiple sclerosis. *J. Neurosci. Res.* 1993, 36, 315-324.
50. Johnson, R. S.; Roder, J. C.; Riordan, J. R. Overexpression of the DM-20 myelin proteolipid causes central nervous system demyelination in transgenic mice. *J. Neurochem.* 1995, 64, 967-976.
51. Moscarello, M. A.; Pritzker, L.; Mastronardi, F. G.; Wood, D. D. Peptidylarginine deiminase: a candidate factor in demyelinating disease. *J. Neurochem.* 2002, 81, 335-343.
52. Carrillo-Vico, A; Leech, M. D.; Anderton, S. M. Contribution of myelin autoantigen citrullination to T cell autoaggression in the central nervous system. *J. Immunol.* 2010, 184, 2839-2846.
53. Suzuki, A; Yamada, R.; Yamamoto, K. Citrullination by Peptidylarginine Deiminase in Rheumatoid Arthritis. *Ann. N. Y. Acad. Sci.* 2007, 1108, 323-339.
54. Arita, K.; Hashimoto, H.; Shimizu, T.; Nakashima, K.; Yamada, M.; Sato, M. Structural basis for Ca(2+)-induced activation of human PAD4. *Nature Struct. Mol. Biol.* 2004, 11, 777-783.
55. Knuckley, B.; Luo, Y.; Thomson, P. R. Profiling protein arginine deiminase 4 (PAD4): A novel screen to identify PAD4 inhibitors. *Bioorg. Med. Chem.* 2008, 16(2), 739-745.
56. Luo, Y.; Knuckley, B.; Lee, Y. H.; Stallcup, M. R.; Thomson, P. R. A fluoroacetamidine-based inactivator of protein arginine deiminase 4: design, synthesis, and in vitro and in vivo evaluation. *J. Am. Chem. Soc.* 2006, 128, 1092-1093.
57. Bello, A. M.; Poduch, E.; Wei, L.; Moscarello, M.; Kotra, L. P. Interrogation of the active site of protein arginine deiminase (PAD) using designer probes. *ACS Med. Chem. Lett.* 2013, 4 (2), 249-253.
58. Wei, L.; Wasilewski, E.; Chakka, S. K.; Bello, A. M.; Moscarello, M. A.; Kotra, L. P. Novel inhibitors of protein arginine deiminase with potential activity in multiple sclerosis animal model. *J. Med. Chem.* 2013, 56 (4), pp 1715-1722.
59. Kearney, P. L.; Bhatia, M.; Jones, N. G.; Yuan, L.; Glascock, M. C.; Catchings, K. L.; Yamada, M.; Thompson, P. R. Kinetic Characterization of Protein Arginine Deiminase 4: A Transcriptional Corepressor Implicated in the Onset and Progression of Rheumatoid Arthritis. *Biochemistry* 2005, 44, 10570-10582.

We claim:

1. A compound of Formula I, or a pharmaceutically acceptable salt or solvate thereof:

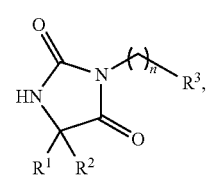

wherein $R^1$ and $R^2$ are independently selected from $C_{1-6}$alkyl and $C_{1-4}$alkylene$R^4$; wherein $R^4$ is selected from COOR$^5$, Ph, $C_{3-6}$cycloalkyl and NHR$^6$; wherein $R^5$ is selected from H and $C_{1-6}$alkyl, and $R^6$ is selected from H, Ac and Bz;

$R^3$ is selected from:

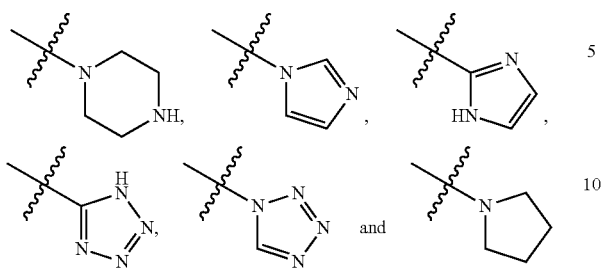

in which any one of the available hydrogen atoms on $R^3$ is optionally substituted with $C_{1-4}$alkyl or cyano; and
n is 1, 2 or 3,
except
when $R^1$ and $R^2$ are $C_{1-2}$alkyl and $R^3$ is piperazinyl, then n does not equal 1 or 2;
when $R^3$ is pyrrolidinyl, n does not equal 1; and
the compound is not

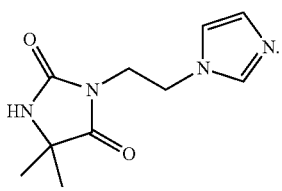 [SMILES: CC1(C)NC(=O)N(CCn2ccnc2)C1=O]

2. The compound of claim 1, wherein $R^1$ and $R^2$ are independently $C_{1-6}$alkyl.

3. The compound of claim 1, wherein $R^1$ and $R^2$ are independently $C_{1-4}$alkylene$R^4$; wherein $R^4$ is selected from COOR$^5$, Ph, $C_{3-6}$cycloalkyl and NHR$^6$; wherein $R^5$ is selected from H and $C_{1-6}$alkyl, and $R^6$ is selected from H, Ac and Bz.

4. The compound of claim 3, wherein $R^1$ and $R^2$ are independently selected from $CH_2COOC_2H_5$, $CH_2COOtBu$, $CH_2CH_2COOH$, $CH_2CH_2CH_2COOH$, $CH_2Ph$, $CH_2CH_2Ph$, $CH_2$-cyclohexyl, $CH_2CH_2NH_2$, $CH_2CH_2CH_2NH_2$, $CH_2CH_2NHAc$, $CH_2CH_2NHBz$, $CH_2CH_2CH_2NHAc$ and $CH_2CH_2CH_2NHBz$.

5. The compound of claim 1, wherein $R^3$ is selected from:

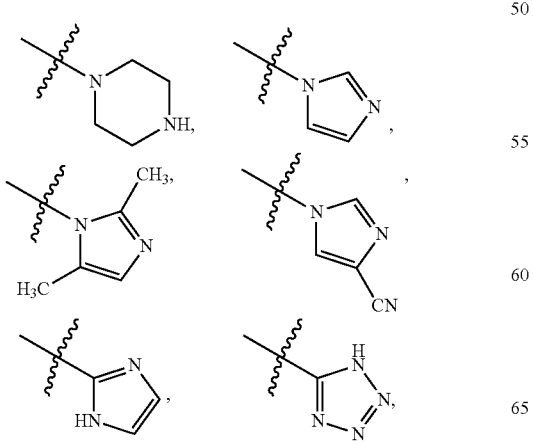

6. The compound of claim 1, wherein $R^3$ is piperazinyl,

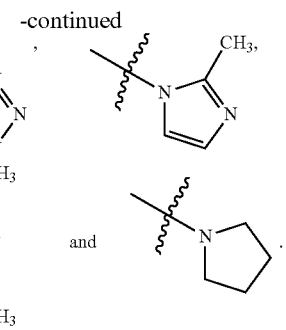

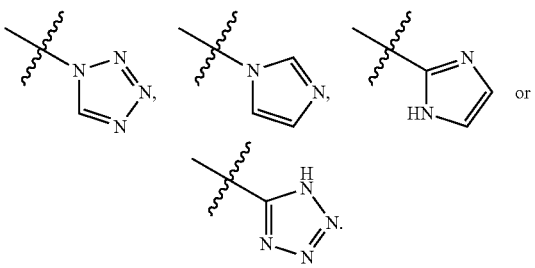

7. The compound of claim 1, which is a compound of Formula (Ib):

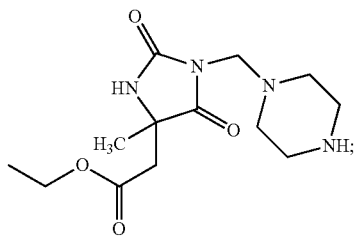

Ib or a compound of Formula (Ic):

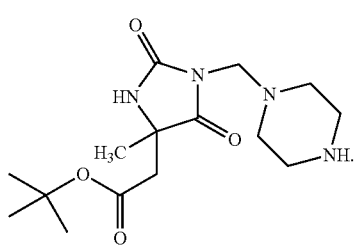

Ic

8. The compound of claim 1, wherein $R^3$ is selected from:

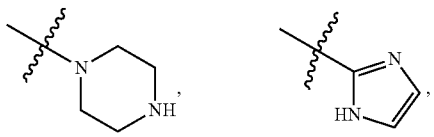

-continued

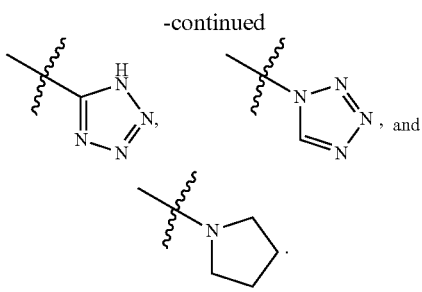

9. The compound of claim 1 that is

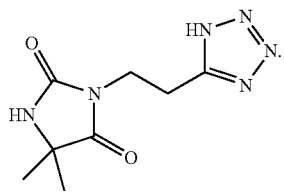 [SMILES: CC1(C)NC(=O)N(CCc2nnn[nH]2)C1=O]

10. A compound of Formula I:

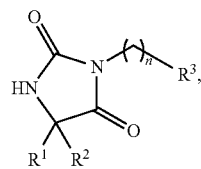

wherein
R¹ and R² are independently selected from $C_{1-6}$alkyl and $C_{1-4}$alkyleneR⁴; wherein R⁴ is selected from COOR⁵, Ph, $C_{3-6}$cycloalkyl and NHR⁶; wherein R⁵ is selected from H and $C_{1-6}$alkyl, and R⁶ is selected from H, Ac and Bz;
R³ is selected from:

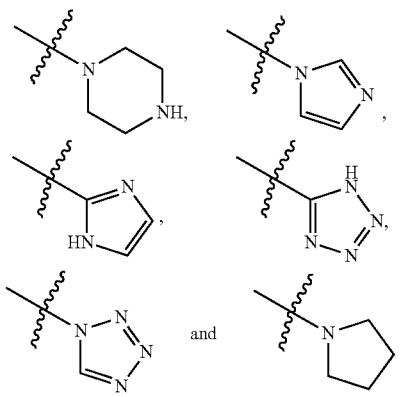

in which any one of the available hydrogen atoms on the carbon atoms of R³ is optionally substituted with $C_{1-4}$alkyl or cyano; and
n is 1, 2 or 3;

except
when R¹ and R² are $C_{1-2}$alkyl and R³ is piperazinyl, then n does not equal 1 or 2; and
when R³ is pyrrolidinyl, n does not equal 1; and
the compound is a pharmaceutically acceptable salt.

11. A method for treating the symptoms of diseases, disorders or conditions characterized by or associated with the hypercitrullination of proteins by peptidyl arginine deiminase (PAD) enzymes comprising administering a therapeutically effective amount of one or more compounds of Formula I to a subject in need thereof, wherein the compound of Formula I is

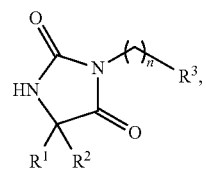

wherein
R¹ and R² are independently selected from $C_{1-6}$alkyl and $C_{1-4}$alkyleneR⁴; wherein R⁴ is selected from COOR⁵, Ph, $C_{3-6}$cycloalkyl and NHR⁶; wherein R⁵ is selected from H and $C_{1-6}$alkyl, and R⁶ is selected from H, Ac and Bz;
R³ is selected from:

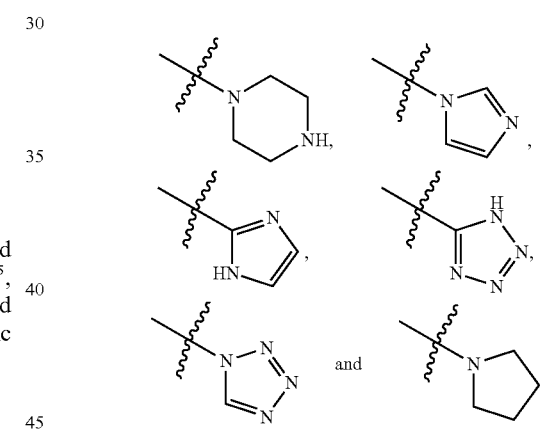

in which any one of the available hydrogen atoms on the carbon atoms of R³ is optionally substituted with $C_{1-4}$alkyl or cyano; and
n is 1, 2 or 3;
except
when R¹ and R² are $C_{1-2}$alkyl and R³ is piperazinyl, then n does not equal 1 or 2; and
when R³ is pyrrolidinyl, n does not equal 1; and
the compound is a pharmaceutically acceptable salt, and wherein the diseases, disorders or conditions characterized by or associated with the hypercitrullination of proteins by PAD enzymes are selected from multiple sclerosis, rheumatoid arthritis, Alzheimer's disease, scrapie, psoriasis and Creutzfeld-Jacob disease.

12. The compound of claim 1, in the form of a pharmaceutically acceptable salt.

13. A pharmaceutical composition comprising one or more compounds of claim 1 and a pharmaceutically acceptable carrier.

14. A method for treating the symptoms of diseases, disorders or conditions characterized by or associated with the hypercitrullination of proteins by peptidyl arginine deiminase (PAD) enzymes comprising administering a therapeutically effective amount of one or more compounds of Formula I, or a pharmaceutically acceptable salt or solvate thereof, to a subject in need thereof, wherein the compound of Formula I is:

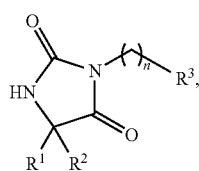

wherein
$R^1$ and $R^2$ are independently selected from $C_{1-6}$alkyl and $C_{1-4}$alkyleneR$^4$; wherein $R^4$ is selected from COOR$^5$, Ph, $C_{3-6}$cycloalkyl and NHR$^6$; wherein $R^5$ is selected from H and $C_{1-6}$alkyl, and $R^6$ is selected from H, Ac and Bz;
$R^3$ is selected from:

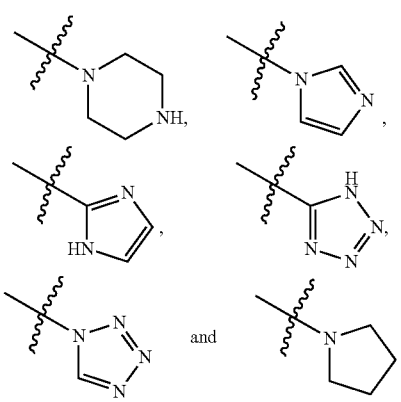

in which any one of the available hydrogen atoms on the carbon atoms of $R^3$ is optionally substituted with $C_{1-4}$alkyl or cyano; and
n is 1, 2 or 3,
except
when $R^1$ and $R^2$ are $C_{1-2}$alkyl and $R^3$ is piperazinyl, then n does not equal 1 or 2;
when $R^3$ is pyrrolidinyl, n does not equal 1; and
the compound is not

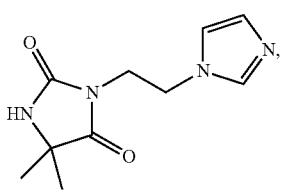 [SMILES: CC1(C)NC(=O)N(CCn2ccnc2)C1=O]

and
wherein the diseases, disorders or conditions characterized by or associated with the hypercitrullination of proteins by PAD enzymes are selected from multiple sclerosis, rheumatoid arthritis, Alzheimer's disease, scrapie, psoriasis and Creutzfeld-Jacob disease.

15. The method of claim 14, wherein $R^1$ and $R^2$ are independently $C_{1-6}$alkyl.

16. The method of claim 14, wherein $R^1$ and $R^2$ are independently $C_{1-4}$alkyleneR$^4$; wherein $R^4$ is selected from COOR$^5$, Ph, $C_{3-6}$cycloalkyl and NHR$^6$; wherein $R^5$ is selected from H and $C_{1-6}$alkyl, and $R^6$ is selected from H, Ac and Bz.

17. The method of claim 16, wherein $R^1$ and $R^2$ are independently selected from $CH_2COOC_2H_5$, $CH_2COOtBu$, $CH_2CH_2COOH$, $CH_2CH_2CH_2COOH$, $CH_2Ph$, $CH_2CH_2Ph$, $CH_2$-cyclohexyl, $CH_2CH_2NH_2$, $CH_2CH_2CH_2NH_2$, $CH_2CH_2NHAc$, $CH_2CH_2NHBz$, $CH_2CH_2CH_2NHAc$ and $CH_2CH_2CH_2NHBz$.

18. The method of claim 14, wherein $R_3$ is selected from:

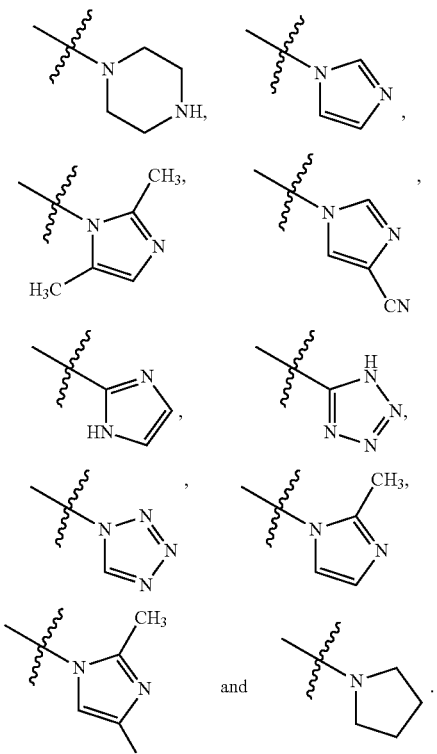

19. The method of claim 14, wherein $R^3$ is piperazinyl,

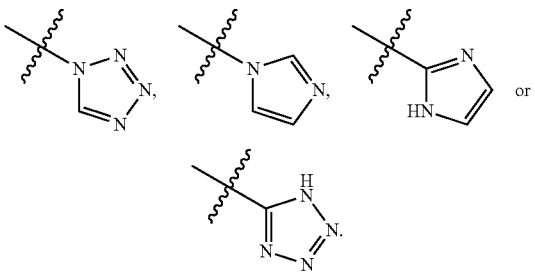

20. The method of claim 14, wherein the compound of Formula I is selected from a compound of Formula I(b) and I(c):

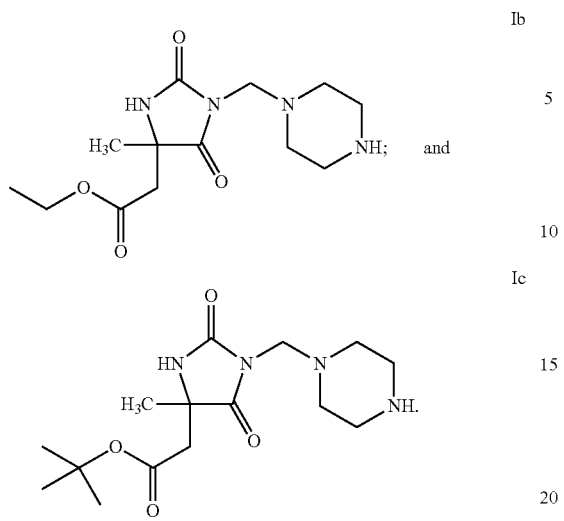
21. The method of claim 14, wherein the compound of Formula I is in the form of a pharmaceutically acceptable salt.
* * * * *

UNITED STATES PATENT AND TRADEMARK OFFICE
CERTIFICATE OF CORRECTION

PATENT NO. : 9,908,853 B2
APPLICATION NO. : 14/418570
DATED : March 6, 2018
INVENTOR(S) : Lakshmi Kotra et al.

It is certified that error appears in the above-identified patent and that said Letters Patent is hereby corrected as shown below:

In the Claims

1. Column 47, Line 15, "atoms on R3" should read --atoms on the carbon atoms of R3--.

Signed and Sealed this
Eleventh Day of December, 2018

Andrei Iancu
*Director of the United States Patent and Trademark Office*